(12) United States Patent
Davies et al.

(10) Patent No.: US 8,480,607 B2
(45) Date of Patent: Jul. 9, 2013

(54) THERAPY FOR LIVER DISEASE

(75) Inventors: Nathan Davies, London (GB); Rajiv Jalan, London (GB)

(73) Assignee: UCL Business PLC, London (GB)

( * ) Notice: Subject to any disclaimer, the term of this patent is extended or adjusted under 35 U.S.C. 154(b) by 615 days.

(21) Appl. No.: 12/312,028

(22) PCT Filed: Oct. 29, 2007

(86) PCT No.: PCT/GB2007/004126
§ 371 (c)(1),
(2), (4) Date: Jun. 19, 2009

(87) PCT Pub. No.: WO2008/050148
PCT Pub. Date: May 2, 2008

(65) Prior Publication Data
US 2010/0025328 A1    Feb. 4, 2010

(30) Foreign Application Priority Data

Oct. 27, 2006   (GB) .................................. 0621452.2

(51) Int. Cl.
*A61M 1/16*     (2006.01)
*A61M 1/34*     (2006.01)

(52) U.S. Cl.
USPC ......................................... 604/5.02; 604/5.04

(58) Field of Classification Search
USPC ....................... 604/5.02; 210/638, 198.1, 646
See application file for complete search history.

(56) References Cited

U.S. PATENT DOCUMENTS

| 4,093,612 | A | 6/1978 | Travis et al. |
| 4,476,715 | A | 10/1984 | Murphy |
| 5,476,715 | A | 12/1995 | Otto |
| 5,744,042 | A * | 4/1998 | Stange et al. ................. 210/645 |
| 5,747,455 | A | 5/1998 | Wainwright et al. |
| 6,365,147 | B1 | 4/2002 | Luo et al. |
| 6,774,102 | B1 | 8/2004 | Bell et al. |
| 7,615,158 | B2 * | 11/2009 | Sternby et al. ................ 210/650 |
| 2003/0229211 | A1 | 12/2003 | Wainwright et al. |
| 2004/0060866 | A1 | 4/2004 | Radunsky et al. |
| 2004/0217055 | A1 * | 11/2004 | Kraus et al. ................... 210/645 |
| 2005/0037331 | A1 | 2/2005 | Galbraith |
| 2006/0019385 | A1 * | 1/2006 | Smith et al. ................... 435/348 |
| 2006/0138049 | A1 * | 6/2006 | Kim et al. ...................... 210/646 |
| 2008/0031874 | A1 * | 2/2008 | Sanders ..................... 424/133.1 |

FOREIGN PATENT DOCUMENTS

| EP | 0 028 937 A2 | 5/1981 |
| EP | 0 129 786 | 2/1990 |
| EP | 0 743 084 A1 | 11/1996 |
| EP | 1 063 289 A1 | 12/2000 |
| EP | 1 220 868 B1 | 7/2002 |
| JP | 8-98883 | 4/1996 |

(Continued)

OTHER PUBLICATIONS

Sen et al., "Emerging Indications for Albumin Dialysis," *Amer. J. of Gastroenterology*, vol. 100, No. 2, pp. 468-475 (2005).

(Continued)

*Primary Examiner* — Susan Su
(74) *Attorney, Agent, or Firm* — Foley & Lardner LLP

(57) ABSTRACT

The invention provides an apparatus for use in the treatment of an individual suffering from liver disease, including: (a) means for selectively removing albumin from the blood of the individual; and (b) means for selectively removing endotoxin from the blood of the individual.

23 Claims, 9 Drawing Sheets

FOREIGN PATENT DOCUMENTS

| | | |
|---|---|---|
| JP | 11-225752 | 8/1999 |
| JP | 2003-299731 | 10/2003 |
| JP | 2003-310752 | 11/2003 |
| JP | 2006-505385 | 2/2006 |
| WO | WO 85/01659 | 4/1985 |
| WO | WO 01/23413 A1 | 4/2001 |
| WO | WO 2004-004707 A1 | 1/2004 |
| WO | WO 2004/082737 A2 | 9/2004 |

OTHER PUBLICATIONS

Liver Support Therapy, "Prometheus: A Life-Saver During Liver Failure," Fresenieus Medical Care Datasheet, 2 pages (2007).

Davies et al., "Serum Albumin Shows Conformational, Structural and Functional Abnormalities in Cirrhotic Patients, which Worsen with Severity of Liver Disease and are Unaffected by Albumin Dialysis," *Hepatology*, vol. 42, No. 4, Suppl. 1, pp. 222A (2005).

Rahman et al., "Review article: Liver Support Systems in Acute Hepatic Failure," *Alimentary Pharm. and Therapeutics*, vol. 13, No. 10, pp. 1255-1272 (1999).

International Search Report for International Application No. PCT/GB2007/004126, May 29, 2008, 5 pgs.

Written Opinion of the International Searching Authority for International Application No. PCT/GB2007/004126, May 29, 2008, 9 pgs.

International Preliminary Report on Patentability for International Application No. PCT/GB2007/004126, Dec. 19, 2008, 11 pgs.

Appen et al., "Microspheres Based Detoxification System: A New Method in Convective Blood Purification," *Artificial Organs*, vol. 20, No. 5, pp. 420-425 (1996).

Bhagavan et al., "Evaluation of Human Serum Albumin Cobalt Binding Assay for the Assessment of Myocardial Ischemia and Myocardial Infarction," *Clinical Chemistry* 49, vol. 4, pp. 581-585 (2003).

Davies et al., "Nitrosyl Heme Production Compared in Endotoxemic and Hemorrhagic Shock," *Free Radic. Biol. Med.*, 38, pp. 41-49 (2005).

Heeman et al., "Albumin Dialysis in Cirrhosis with Superimposed Acute Liver Injury: A Prospective, Controlled Study," *Hepatology*, vol. 36, No. 4, pp. 949-958 (2002).

Hwang et al., "Lipopolysaccharide-Binding and Neutralizing Activities of Surfactin C in Experimental Models of Septic Shock," *European Journ. of Pharm.*, vol. 556, pp. 166-171 (2007).

Jaeschke et al., "Role of Neutrophils in Acute Inflammatory Liver Injury," *Liver International*, vol. 26, pp. 912-919 (2006).

Jalan et al., "Acute-on-Chronic Liver Failure: Pathophysiological Basis of Therapeutic Options," *Blood Purif.*, vol. 20, pp. 252-261 (2002).

Jalan et al., "Reversal of Diuretic-Induced Hepatic Encephalopathy with Infusion of Albumin but not Colloid," *Clinical Science*, vol. 106, pp. 467-474 (2004).

Kohler et al., Continuous Cultures of Fused Cells Secreting Antibody of Predefined Specificity, *Nature*, vol. 256, pp. 495-497 (1975).

Maddox et al., "Elevated Serum Levels in Human Pregnancy of a Molecule Immunochemically Similar to Eosinophil Granule Major Basic Protein," *J. Exp. Med.*, vol. 158, pp. 1211-1219 (1983).

Mookerjee et al., "Neutrophil Dysfunction in Alcoholic Hepatitis Superimposed on Cirrhosis is Reversible and Predicts the Outcome," *Hepatology*, vol. 46, No. 3, pp. 831-840 (2007).

Quinlan et al., "Albumin: Biochemical Properties and Therapeutic Potential," *Hepatology*, vol. 41, No. 6, pp. 1211-1219 (2005).

Roy et al., "Ischemia-Modified Albumin Concentrations in Patients with Peripheral Vascular Disease and Exercise-Induced Skeletal Muscle Ischemia," *Clinical Chemistry*, vol. 50, No. 9, pp. 1656-1660 (2004).

Sen et al., "The Pathophysiological Basis of Acute-on-Chronic Liver Failure," *Liver*, vol. 22(Suppl. 2), pp. 5-13 (2002).

Sen et al., "Pathophysiological Effects of Albumin Dialysis in Acute-on-Chronic Liver Failure: A Randomized Controlled Study," *Liver Transplantation*, vol. 10, No. 9, pp. 1109-1119 (2004).

Sort et al., "Effect of Intravenous Albumin on Renal Impairment and Mortality in Patients with Cirrhosis and Spontaneous Bacterial Peritonitis," *N. Engl. J. Med.*, vol. 341, No. 6, pp. 403-409 (1999).

Stadbauer et al., "Endotoxin Measures in Patients' Sample: How Valid Are the Results?", *Journ. Of Hepatology*, vol. 47, pp. 726-731 (2007).

Staubach et al., "A New Endotoxin Adsorption Device in Gram-Negative Sepsis: Use of Immobilized Albumin with the MATISSE® Adsorber," *Transfusion and Apheresis Science*, vol. 29, pp. 93-98 (2003).

Wright et al., "Endotoxemia Produces Coma and Brain Swelling in Bile Duct Ligated Rats," *Hepatology*, vol. 45, pp. 1517-1526 (2007).

The Japanese Notice of Reasons for Rejection received in the related Japanese Patent Application 2009-533950, dated Sep. 4, 2012. (with English Translation).

\* cited by examiner

THERAPY FOR LIVER DISEASE

CROSS-REFERENCE TO RELATED APPLICATIONS

This application is the U.S. National Phase of International Patent Application No. PCT/GB2007/004126, filed on Oct. 29, 2007, which claims the benefit of priority from Great Britain Application No. 0621452.2, filed on Oct. 27, 2006. The contents of these applications are incorporated herein by reference in their entirety.

FIELD OF THE INVENTION

The invention relates to the treatment of an individual suffering from liver disease. It relates to methods for the treatment of such an individual and to systems and devices for use in such treatment.

BACKGROUND TO THE INVENTION

In the United States alone it is estimated that 60,000 people die each year of liver failure, whereas the donor pool remains constant at approximately 4000 with 16-18,000 on the waiting list. The odds of receiving a donor liver for subjects waiting on the list are only 1 in 8, yet there is no effective treatment available to extend the lifetime of this group of patients.

Liver failure results in multiple organ dysfunction and mortality rates are in the order of 80%. In patients with cirrhosis, the main precipitant of acute deterioration in liver function is infection. The specific form of infection that is most commonly observed in such patients is spontaneous bacterial peritonitis. This acute deterioration in end-organ function continues despite treatment of the underlying infection and mortality rates of up to 40% are commonly observed. However, the mechanisms that lead to this acute deterioration in liver function following infection are not clear.

SUMMARY OF THE INVENTION

The invention relates to the treatment of liver disease and addresses two crucial factors which may influence morbitity and mortality, namely defects in albumin structure, function and levels in patients with liver disease, and increased levels of endotoxin in the blood of such patients.

Accordingly, the invention provides an apparatus for use in the treatment of an individual having liver disease, comprising:
  (a) means for selectively removing albumin from the blood of an individual; and
  (b) means for selectively removing endotoxin from the blood of an individual;

The invention also provides:

A method of treating an individual having liver disease comprising the steps of:
  (a) removing albumin from the blood of the individual; and
  (b) reducing the level of endotoxin in the blood of the individual.

A method of treating liver disease comprising the steps of contacting blood from an individual with an apparatus of the invention such that albumin and endotoxin are removed from the blood of the individual.

A method of treating blood extracorporeally by selectively removing albumin and endotoxin from the blood, wherein the blood is from an individual having liver disease.

| day     | 20 | 40 | 60 | 80 |
|---------|----|----|----|----|
| events  | 4  | 5  | 10 | 12 |
| at risk | 50 | 44 | 36 | 33 |

Figure 4:
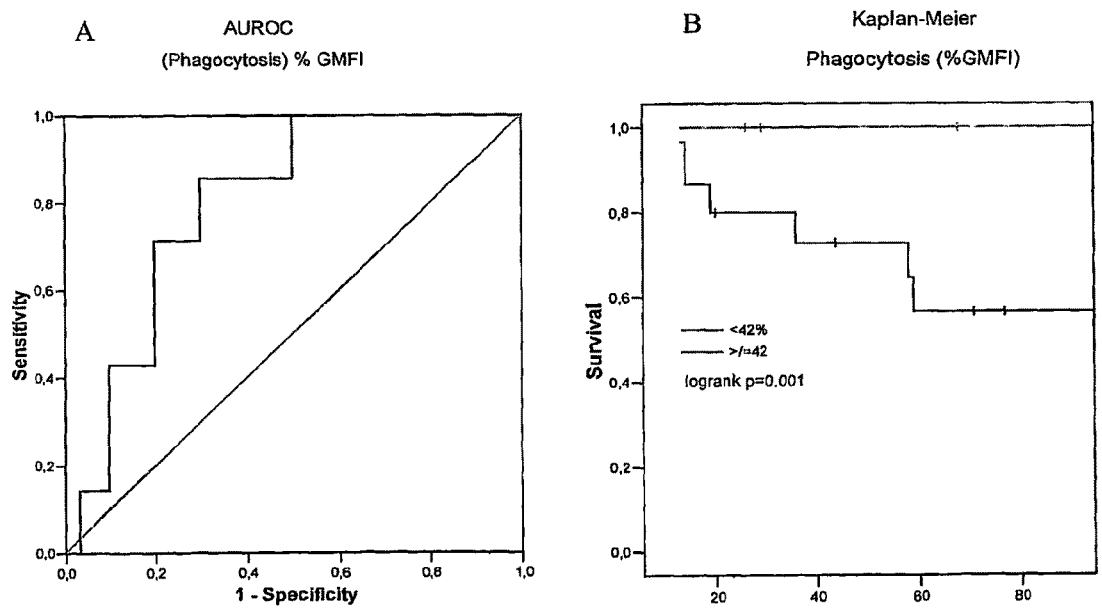

FIG. 4: (A) Area under the receiver operating curve to determine the predictive utility of measurement of the geometric mean of fluorescence intensity (GMFI) in determining survival. A cutoff of GMFI <295% had a sensitivity of 86% and a specificity of 76% for predicting death. Area=0.80; Std Erros=0.08; significance=0.02; cut-off=42; sensitivity=0.86; specificity=0.70. (B) Kaplan Meier survival curve and log-rank analysis for patients stratified for low (<42) or high (>/=42) GMFI.

| day     | 20 | 40 | 60 | 80 |
|---------|----|----|----|----|
| events  | 4  | 4  | 5  | 5  |
| at risk | 29 | 29 | 26 | 24 |

Figure 5:
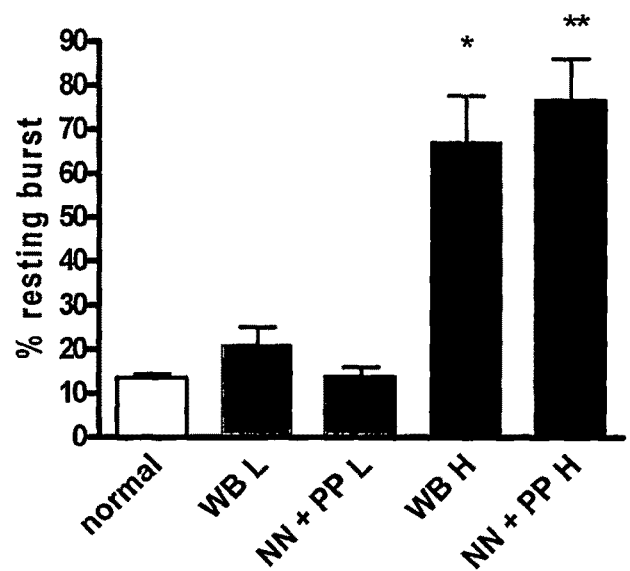

FIG. 5: Resting oxidative burst in whole blood of patients and in normal neutrophils incubated with patients plasma. Plasma from patients with high burst also induced a high burst in normal neutrophils, whereas plasma from patients with low resting burst failed to do so. WB whole blood, NN normal neutrophils, PP patients plasma, H high resting burst (>/=55%), L Low resting burst (<55%). *p=0.002 vs. normal. **p=0.0005 vs. normal.

Figure 6:
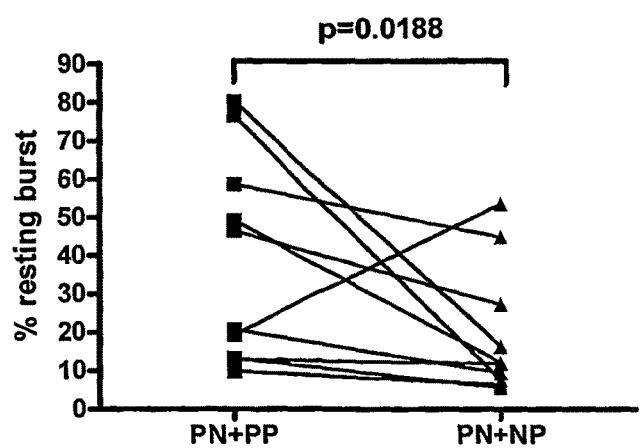

FIG. 6: Reversibility of resting oxidative burst by incubation of patients neutrophils with normal plasma. PN patient neutrophils, PP patient plasma, NP normal plasma.

Figure 7:
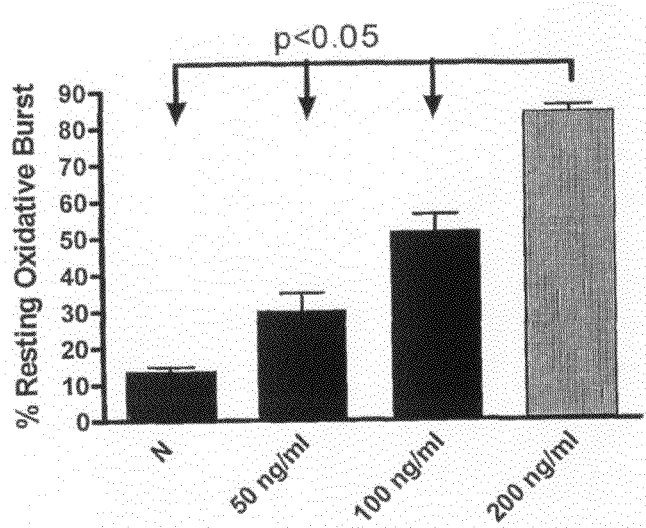

FIG. 7: Dose dependent increase in resting burst through incubation with endotoxin. *p<0.05; **p<0.001.

Figure 8:
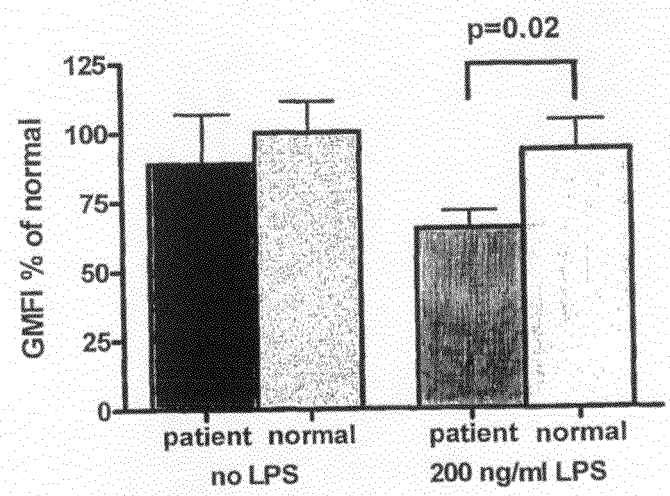

FIG. 8: Incubation with endotoxin does not change phagocytosis in normal neutrophils but decreases phagocytosis further in patients neutrophils.

Figure 9:
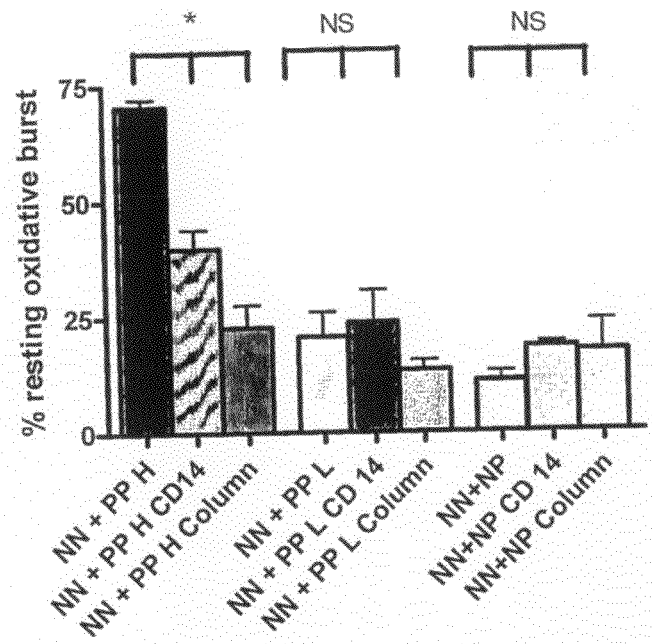

FIG. 9: Resting oxidative burst is reversible by passing plasma over an endotoxin-removal column or incubation with CD14 antibodies. The columns or the CD 14 antibodies do not influence resting burst when plasma from patients with low burst or control plasma is used. NN+PP H vs. NN+PP H CD14 p<0.001. NN+PP H vs. NN+PP HB Column p<0.001.

Figure 10:
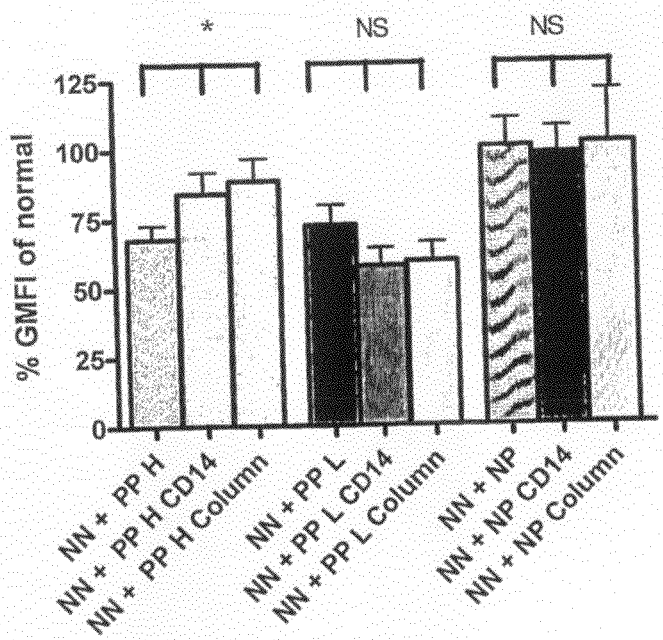

FIG. 10: Decreased phagocytosis is reversible by passing plasma over an endotoxin-removal column or incubation with CD14 antibodies. The columns or the CD 14 antibodies do not influence resting burst when plasma from patients with low burst or control plasma is used. NN+PP H vs. NN+PP H CD14 p=0.04 NN+PP H vs. NN+PP HB Column p=0.03.

Figure 11:
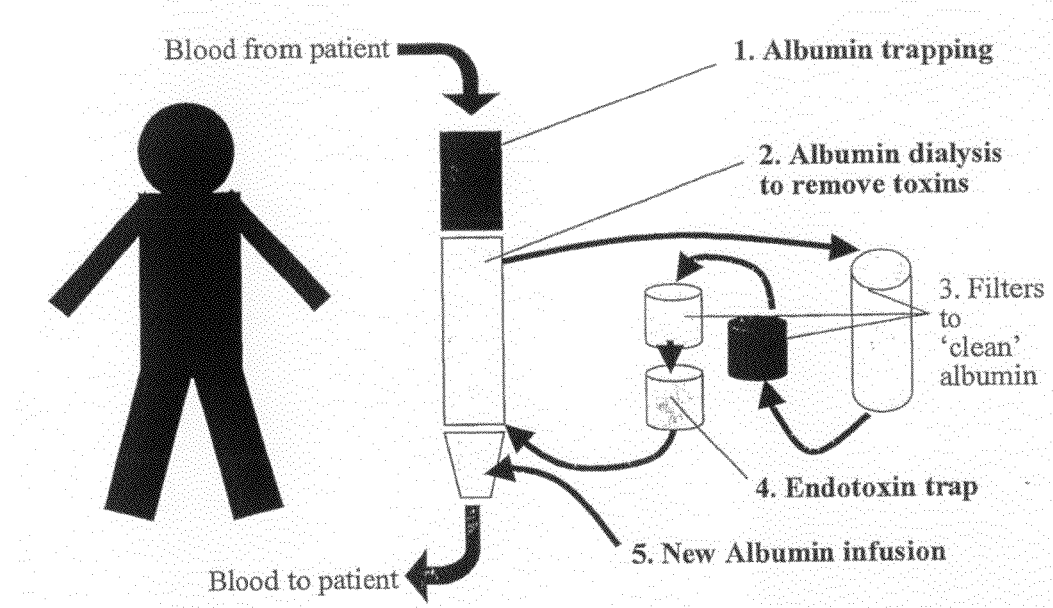
Figure 11:
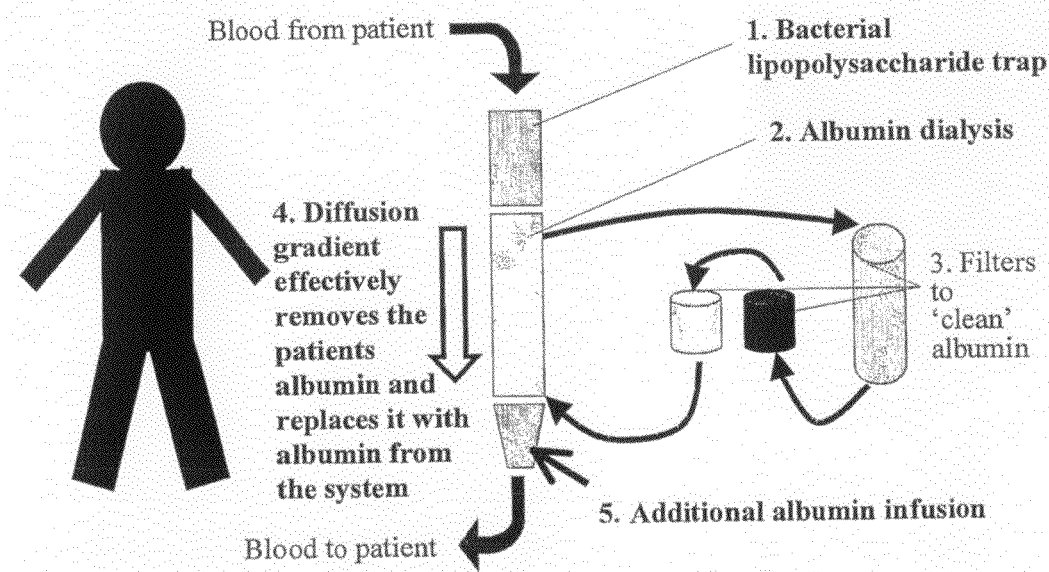

FIG. 11: Illustration of albumin replacement systems.

Figure 12:
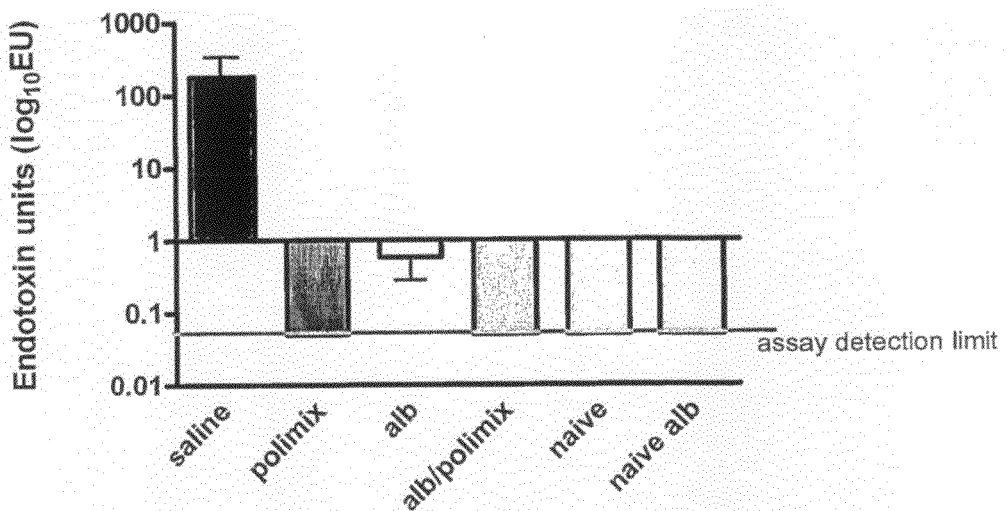

FIG. 12: Measured endotoxin levels in plasma samples collected at the termination of the experiment in Example 3 (T=3hours). Significantly higher endotoxin level (p<0.001) was found in the saline treated animals compared to all other groups. According to the manufacturer the detection limit of this assay is 0.5 EU/ml, as indicated in the figure.

Figure 13A:
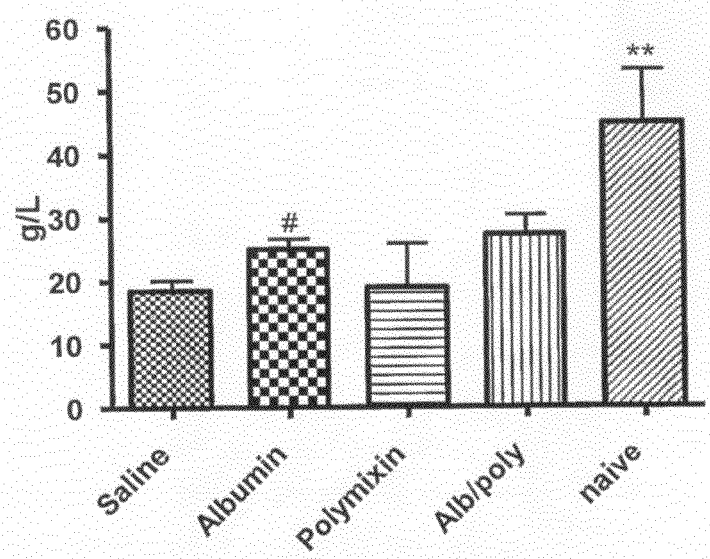
Figure 13B:
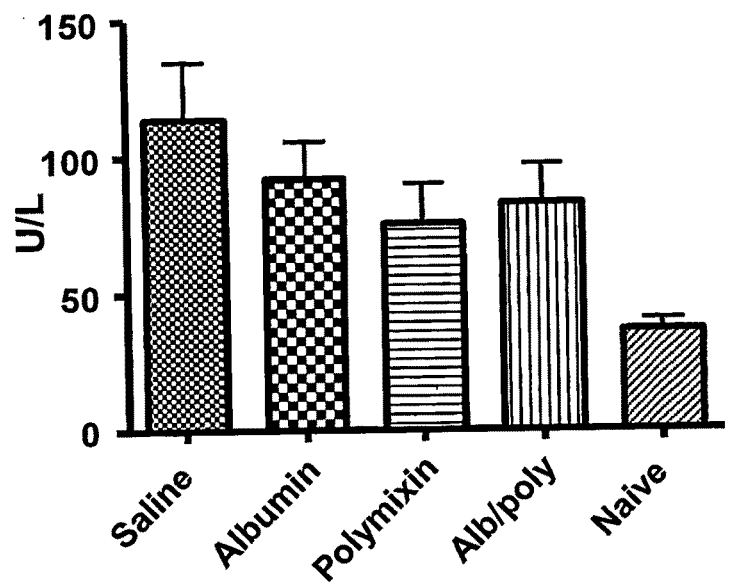

FIG. 13: Levels measured in blood samples collected at the termination of the experiment in Example 3:
A: Albumin levels. Albumin was found to be significantly reduced at 4 weeks following BDL surgery (**p<0.01 vs naïve animals), but was markedly increased following albumin therapy (# p<0.05 vs saline, Mann-Whitney test).
B: Plasma ALT levels. Though there was apparent reduction in plasma ALT in all treatment groups compared with the animals given saline, these differences did not prove to be significant.
C: Plasma urea concentration. It was found that animals receiving the combination of albumin and polymixin B had significantly lower urea levels compared to the group administered albumin alone (*p<0.05, Mann-Whitney test).

Figure 14:
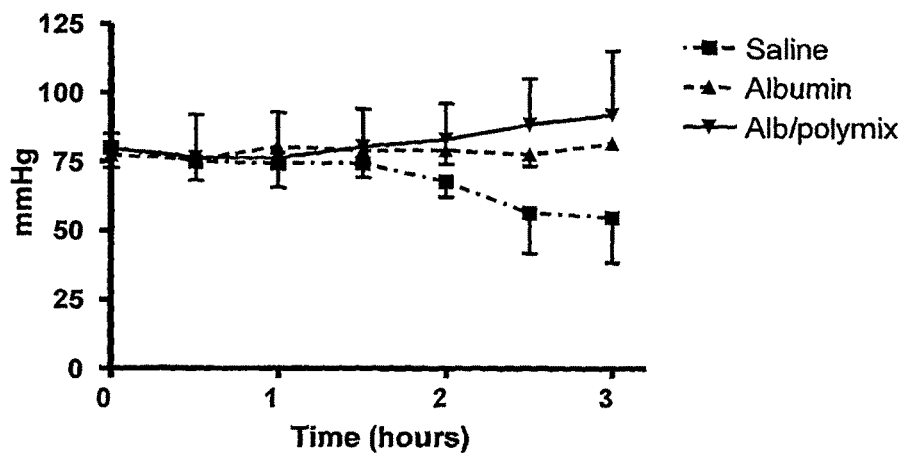

FIG. 14. Measured mean arterial pressure (MAP) throughout the time course of the study in Example 3. Though the difference was not found to be significant, it appears as though the group receiving the combined albumin/polymixin therapy had improved MAP compared with animals receiving albumin alone, both of which were superior to the saline treated group which demonstrated a noticeable deterioration after 90 minutes.

Figure 15:
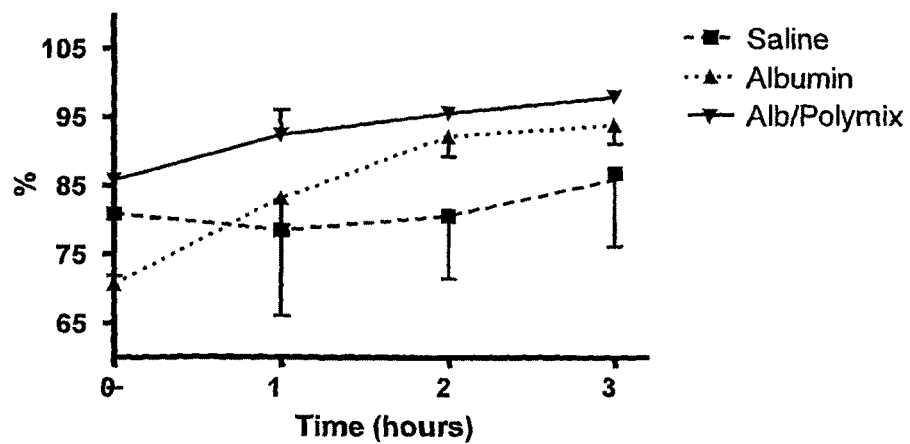

FIG. 15. Neutrophil activity in arterial blood samples collected throughout the experimental period. Y axis shows the % of neutrophils bursting in response to bacteria. It can be seen that the percentage of neutrophils creating oxidative burst in response to pathogenic bacteria progressively increases in both the albumin and albumin/polymixin treated groups over the tie course of the study. A slight improvement is observed in the saline treated animals at 3 hours but this was lower than the other groups and not found to be significant.

DETAILED DESCRIPTION OF THE INVENTION

Throughout this specification, the word "comprise", or variations such as "comprised" or "comprising", will be understood to imply the inclusion of a stated element, integer or step, or group of elements, integers or steps, but not the exclusion of any other element, integer or step, or group of elements, integers or steps.

The reference to any prior art in this specification is not, and should not be taken as, an acknowledgement or any form of suggestion that that prior art forms part of the general knowledge in Australia or elsewhere.

Currently, the range of treatments available for patients with liver disease, particularly those patients with liver failure, is limited. For many patients the only option is transplant, yet there is no effective treatment available to extend the lifetime of this group of patients. There is thus a need to find treatment regimes which can be used to improve the condition of individuals suffering from liver disease.

Albumin is the major plasma protein that is produced in the liver. Albumin undertakes a variety of functions including fatty acid transport, metal chelation, drug binding and antioxidant activity. In liver disease its concentration is diminished either due to decreased synthesis or resulting from higher degradation rates. The present inventors have additionally shown that in patients having liver disease, a proportion of the albumin in the blood circulation is structurally abnormal. The inventors have also found that the amount of ischaemia modified albumin (IMA) is increased in patients with liver disease compared with healthy control subjects. The functional ability of a proportion of the albumin from the patient with liver failure is permanently destroyed.

In one aspect, therefore, the invention relates to the removal of albumin from the blood of an individual having liver disease.

Removal of albumin in this context refers to the removal of structurally normal albumin, and also to the removal of any structurally or functionally modified forms of albumin present in the blood of the individual. That is, preferably, the means for removing albumin used in accordance with the present invention will be capable of removing not only normal, naturally occurring albumin, but also albumin which may have an abnormal structure or albumin which has been modified. Removal of any damaged or abnormal albumin may also be therapeutically useful because damaged albumin has poor functionality and may be associated with damaging side reactions. For example, the means for removing albumin may also remove albumin having reduced molecular flexibility, reduced fatty acid binding affinity, reduced transport quality, reduced transport efficiency and/or reduced detoxification ability compared with normal, unmodified albumin. The means for removing albumin may also remove particular modified forms of albumin, such as ischaemia modified albumin (IMA). Such structural and functional modifications may be detected using conventional techniques, for example as described in Example 1. In particular, albumin functionality may be assessed using a spin label and electron paramagnetic resonance spectroscopy. The presence of IMA may be detected by examining the ability of the albumin to bind metal atoms.

Removal of albumin may also detoxify the blood by removing any associated albumin-bound toxins. That is, the means for removing albumin may also consequently remove toxins in the blood that are bound to the albumin.

Preferably, the means for removing albumin from the blood removes albumin selectively. That is, albumin is removed in preference to other substances in the blood, such as other proteins. Preferably the amount of albumin removed from the blood is significantly greater than that of other blood components removed. For example, more than 99% by weight of the component removed in this aspect may be albumin. More than 98%, more than 95%, more than 90%, more than 80%, more than 70%, more than 60% or more than 50% of the component removed in this aspect may be albumin. Removal of albumin here includes the removal of the various modified forms of albumin described herein.

The means for removing albumin may be any means capable of selectively removing albumin from blood.

In one aspect, albumin is selectively removed using a ligand that binds the albumin. The ligand may be any molecule that binds albumin. For example, a number of reactive dyes are known to bind albumin. The ligand may be an antibody or other affinity ligand that specifically binds albumin. Typically, a ligand that specifically binds albumin is a ligand capable of selectively removing albumin from blood as explained above. For example, the ligand may be capable of binding albumin more strongly than other components of blood. For example, the ligand may be an antibody that specifically binds human albumin. The ligand may be an antibody that binds an epitope that is specific to albumin. The ligand may be a combination of molecules which each bind albumin, such as a combination of molecules which bind different parts of the albumin molecule. The ligand may be a polyclonal antibody or mixture of antibodies which bind to multiple epitopes on the albumin protein. Such a combination approach may be useful in the removal of modified forms of albumin as different antibodies may target different parts of the albumin molecule.

Antibodies may be raised against specific epitopes of the albumin molecule. For example, antibodies may be raised specifically against those regions, which are expected to be structurally similar in unmodified and particular modified forms of albumin.

For the purposes of this invention, the term "antibody", unless specified to the contrary, includes fragments which bind albumin. Such fragments include Fv, F(ab') and F(ab')$_2$ fragments, as well as single chain antibodies. Furthermore, the antibodies and fragment thereof may be chimeric antibodies, CDR-grafted antibodies or humanised antibodies.

Antibodies for use in the present invention can be produced by any suitable method. Means for preparing and characterising antibodies are well known in the art, see for example Harlow and Lane (1988) "Antibodies: A Laboratory Manual", Cold Spring Harbor Laboratory Press, Cold Spring Harbor, N.Y. For example, an antibody may be produced by raising antibody in a host animal against the whole polypeptide or a fragment thereof, for example an antigenic epitope thereof, herein after the "immunogen".

A method for producing a polyclonal antibody comprises immunising a suitable host animal, for example an experimental animal, with the immunogen and isolating immunoglobulins from the animal's serum. The animal may therefore be inoculated with the immunogen, blood subsequently removed from the animal and the IgG fraction purified.

A method for producing a monoclonal antibody comprises immortalising cells which produce the desired antibody. Hybridoma cells may be produced by fusing spleen cells from an inoculated experimental animal with tumour cells (Kohler and Milstein (1975) *Nature* 256, 495-497).

An immortalized cell producing the desired antibody may be selected by a conventional procedure. The hybridomas may be grown in culture or injected intraperitoneally for formation of ascites fluid or into the blood stream of an allogenic host or immunocompromised host. Human antibody may be prepared by in vitro immunisation of human lymphocytes, followed by transformation of the lymphocytes with Epstein-Barr virus.

For the production of both monoclonal and polyclonal antibodies, the experimental animal is suitably a goat, rabbit, rat or mouse. If desired, the immunogen may be administered as a conjugate in which the immunogen is coupled, for example via a side chain of one of the amino acid residues, to a suitable carrier. The carrier molecule is typically a physiologically acceptable carrier. The antibody obtained may be isolated and, if desired, purified.

An antibody, or other ligand, "specifically binds" to a protein when it binds with preferential or high affinity to the protein for which it is specific but does substantially bind not bind or binds with only low affinity to other proteins. That is, an antibody specifically binds albumin if it binds to albumin more strongly than it binds to other blood components, such as other proteins in the blood. As explained above, the specificity of binding may be such that it binds structurally or functionally altered forms of albumin as well as unmodified albumin. Preferably it binds structurally or functionally altered forms of albumin with the same or substantially the same binding affinity as unmodified albumin. Preferably, it binds both modified and unmodified forms of albumin with a greater affinity than other blood components, such as other proteins in the blood. A variety of protocols for competitive binding or immunoradiometric assays to determine the specific binding capability of an antibody are well known in the art (see for example Maddox et al, J. Exp. Med. 158, 1211-1226, 1993). Such immunoassays typically involve the formation of complexes between the specific protein and its antibody and the measurement of complex formation.

Where a ligand is used to achieve removal of albumin, the ligand may be provided attached to a solid support. The ligand may be immobilised on such a solid support. A suitable solid support may be in the form of a column through which the blood may be passed. A suitable solid support may be, for example, a porous material such as a membrane, particle bed or filter which is sufficiently porous to allow blood cells to pass through it. A suitable solid support may alternatively be a solid substrate across the surface of which blood may be passed. Preferably the solid support has a large surface area to maximise the area of contact between the blood of the individual and the ligand attached to the support. The solid support may be in the form of beads, which can be filled into a container into which the blood can be inserted, or through which the blood can be passed. The beads will preferably have a size sufficient to allow sufficient porosity when packed into a column or filter bed. Various bead materials are known in the art.

Accordingly, the means for removing albumin according to the present invention may comprise or consist of such a solid support on which is attached or immobilised a ligand capable of binding albumin. The means for removing albumin may comprise or consist of a container through which blood is passed. The container may thus comprise an inlet and an outlet. The inlet and outlet are positioned so that blood passing through the container comes into contact with a solid support as described herein. Preferably the means for removing albumin is designed or selected to maximise the area of contact between the blood and the solid support. A variety of such designs are known in the art. For example, the means for removing albumin may be a column or filter bed packed with beads, wherein a ligand for albumin is immobilised on the beads.

In another aspect, removal of albumin may be achieved via dialysis. Such an approach may also lead to the removal of other blood components that are dialysed together with the albumin. Typically, albumin should be the predominant component removed. This dialysis step can use any albumin dialysis system. A variety of such systems are known in the art. One such system is the molecular absorbance recirculating system (MARS). An alternate is a generic single pass albumin dialysis (SPAD) system. These systems use a 50 kDa pore membrane to dialyse albumin in blood. This system is designed particularly to remove albumin-bound toxins from the blood of patients.

As an alternative to this system, a larger pore membrane can be utilised so that albumin from the patients blood is actively exchanged with fresh albumin via dialysis. This permits the removal of toxins and abnormal forms of albumin in the same step. This also allows the introduction into the blood of new albumin, not from the individual, as discussed further below.

Studies in which the MARS system is modified to include a larger pore membrane indicate that there is a substantial improvement in protein-bound toxin removal compared to the standard 50 kDa pore device. For example, a membrane having a pore size of greater than 50 kDa, greater than 60 kDa, greater than 70 kDa, greater than 80 kDa, greater than 90 kDa or greater than 100 kDa may be used. The membrane may have a pore size of less than 60 kDa, less than 75 kDa, less than 100 kDa or less than 150 kDa.

Other blood components may be removed together with albumin depending on the particular means used to remove the albumin. In one embodiment, other components which are removed with the albumin may be returned to the blood of the individual. The components to be returned may be purified from the albumin mixture that has been removed from the blood, or may be replaced by fresh equivalent components not deriving from the individual.

Various methods of removing albumin from the blood are known in the art. For example, U.S. Pat. No. 4,093,612 discloses reactive dye compositions that can be used to remove albumin from a fluid. In accordance with the present invention, such compositions may be used for the removal of albumin from the blood of the individual. This may therefore be a selective albumin trapping system based on compounds which specifically bind albumin. These may be, for example reactive dyes as described in U.S. Pat. No. 4,093,612 such as cibacron-blue, or may be other molecules capable of binding albumin, such as albumin-specific antibodies.

In accordance with the present invention therefore, albumin is removed from the blood of an individual with liver disease. In one aspect, this albumin may be replaced with new albumin which does not derive from the individual. The new albumin is preferably structurally and functionally normal. That is, the new albumin may comprise no, or substantially no, structurally or functionally modified forms of albumin. Where albumin removed from the blood of an individual comprises one or more modified forms of albumin, the albumin returned to the blood of that individual preferably comprises less modified albumin than has been removed. For example, the albumin returned to the blood of the individual may comprise less than 50%, less than 30%, less than 20%, less than 10%, less than 5% or less than 1% of the amount of modified albumin removed from that individual. Preferably, the albumin returned to the individual will comprise no modified albumin or no modified albumin of one or more of the types that were removed from the individual, such as no ischaemia modified albumin (IMA).

The new albumin may derive from another individual, such as an individual that does not have liver disease, an individual that does not have liver failure or an individual that has normal liver function. The new albumin may be albumin that has been removed from the individual, but has been cleaned or purified to remove toxins and/or modified albumin molecules. The new albumin will typically have a higher proportion of structurally and functionally normal albumin than the albumin removed from the individual. The new albumin can be pharmaceutical grade albumin.

This new albumin is introduced into the blood of the individual to ensure that the individual has a suitable level of circulating albumin. This can be a direct replacement for the albumin removed, for example, the same or an equivalent amount of albumin to that that is removed can be returned to the blood. In this system, the individual's albumin is effectively exchanged with new albumin. Alternatively, by varying the amount of albumin introduced at this stage, the overall albumin concentration in the blood can be increased or decreased if necessary. The amount of albumin that is introduced to the blood may thus be greater than or less than the amount that is removed. For example, liver disease can lead to a decrease in the level of circulating albumin. This can result in a low functional capacity. In accordance with the present invention the amount of new albumin introduced to the blood of the patient may be greater than the amount of albumin removed. This may supplement the level of albumin in the circulation of the individual. For example, an amount of new albumin may be introduced which raises the overall albumin level in the blood to a level the same as, or similar to, that seen in an individual not having liver disease.

The fresh albumin may be introduced to the blood of the individual simultaneously with the removal of the individual's albumin. For example, an exchange of albumin may be achieved by dialysis. Alternatively, the steps of albumin removal and albumin return may be carried out sequentially or separately. For example, where the invention is carried out ex vivo, the blood of the individual may be passed through means for removing albumin and then subsequently have fresh albumin added to it. This may be achieved by different parts of the same apparatus. Alternatively the addition of fresh albumin may be carried out separately. Typically the addition of fresh albumin is carried out after the removal of albumin from the patient's blood.

In further studies described herein, the inventors have shown that endotoxin is a component in the blood of individuals with liver disease which may be associated with the prognosis of those patients, for example their susceptibility to infection or organ failure, their risk of mortality and their potential responsiveness to some therapies such as immunosuppression.

The inventors have found that these prognosis factors are linked to activation of neutrophils in the blood of an individual having liver disease, and that such activation may be related to the presence of a transmissible factor in the plasma of those individuals. Thus, plasma from an individual having a high degree of neutrophil activation is capable of increasing the level of activation of normal neutrophils.

The inventors have further found that a similar effect may be achieved by contacting normal neutrophils with endotoxin, and that removal of endotoxin from the blood of patients having a high degree of neutrophil activation can reduce the activation levels of neutrophils in that blood. Removal of endotoxin is therefore believed to be useful in the treatment of patients having liver disease whose neutrophils are in an activated state. By restoring normal neutrophil function, the ability of those individuals to combat infection may be improved.

Accordingly, the present invention also relates to the removal of endotoxin from the blood of the patients. Removal of albumin addresses one issue of detoxification, removal of endotoxin relates to a further issue of reduced immune response. By combining these two approaches in a single apparatus or method, a particularly effective treatment of liver disease is achieved.

Preferably, the means for removing endotoxin from the blood removes endotoxin selectively. That is, endotoxin is removed in preference to other substances in the blood. Preferably the amount of endotoxin removed from the blood is significantly greater than that of other blood components removed. For example, more than 99% by weight of the component removed in this aspect may be endotoxin. More than 98%, more than 95%, more than 90%, more than 80%, more than 70%, more than 60% or more than 50% of the component removed in this aspect may be endotoxin.

The means for removing endotoxin may be any means capable of selectively removing endotoxin from blood.

In one aspect, endotoxin may be selectively removed using a ligand that binds the endotoxin. The ligand may be any molecule that binds endotoxin. For example, anti-endotoxin antibodies, LPS binding proteins, Polymyxin B, polyethyleneimine, an arginine ligand and various peptides are known to bind endotoxin. The ligand may be an antibody or other affinity ligand that specifically bind endotoxin. For example, the ligand may be an antibody that specifically binds endotoxin. Typically, a ligand that specifically binds endotoxin is a ligand capable of selectively removing endotoxin from blood as explained above. For example, the ligand is capable of binding endotoxin more strongly than other components of blood. The ligand may be an antibody that binds an epitope that is specific to endotoxin. The ligand may be a combination of molecules which each bind endotoxin, such as a combination of molecules which bind different parts of the endotoxin molecule or different endotoxins. The ligand may be a polyclonal antibody or mixture of antibodies which bind to multiple epitopes on the endotoxin molecule or different endotoxins.

Antibodies may be raised against specific epitopes of the endotoxin molecule. Suitable antibody types may be any antibody type, as described above in relation to albumin, such as an antibody fragment.

Antibodies that bind endotoxin may be prepared by any means, for example as described above in relation to albumin-binding antibodies. The antibody obtained may be isolated and, if desired, purified.

An antibody, or other ligand, "specifically binds" to a protein when it binds with preferential or high affinity to the protein for which it is specific but does substantially bind not bind or binds with only low affinity to other proteins. That is, it binds to endotoxin more strongly than it binds to other blood components, such as other proteins in the blood. The specificity of binding may be such that it binds different forms of endotoxin. Preferably, it binds a variety of forms of endotoxin with a greater affinity than other blood components.

Where a ligand is used to achieve removal of endotoxin, the ligand may be provided attached to a solid support. The ligand may be immobilised on such a solid support. Suitable solid supports are as discussed above in relation to albumin-binding ligands.

Accordingly, the means for removing endotoxin according to the present invention may comprise or consist of such a solid support on which is attached or immobilised a ligand capable of binding endotoxin. The means for removing endotoxin may comprise or consist of a container through which blood is passed. The container may thus comprise an inlet and an outlet. The inlet and outlet are positioned so that blood passing through the container comes into contact with a solid support as described herein. Preferably the means is designed or selected to maximise the area of contact between the blood and the solid support. A variety of such designs are known in the art. For example, the means may be a column or filter bed packed with beads, wherein a ligand for albumin is immobilised on the beads.

In another aspect, rather than physically removing the endotoxin from the blood, an agent may be administered to the individual to reduce endotoxin levels. For example the endotoxin in the blood may be functionally neutralised rather than removed. Various methods for neutralising endotoxin are known in the art. This may comprise administering an agent to the individual, which agent is capable of selectively removing or neutralising the activity of the endotoxin. This may rely on the host immune system to aid removal of endotoxin. For example, a suitable agent may bind endotoxin and allow the immune system of the individual to clear the endotoxin-agent complexes from the blood. Various agents for decreasing circulating endotoxin levels are known, for example anti-endotoxin antibodies, albumin and LPS-binding proteins, LPS neutralising CD-14 antibodies.

Other blood components may be removed together with endotoxin depending on the particular means used to remove the endotoxin. For example, some methods for removing endotoxin may also remove other toxins from the blood. This may be beneficial to the patient. Some methods for removing endotoxin may also remove other blood components which it is desired to maintain in the blood. In this case, blood components which are removed with the endotoxin may be returned to the blood of the individual. The components to be returned may be purified from the endotoxin mixture removed, or may be replaced by fresh equivalent components that do not derive from the individual.

Various approaches for removing endotoxin from a sample have been described in the art. For example, EP-A-0 129 786 describes the use of Polymyxin B covalently immobilized on polystyrene fibres for the removal of endotoxins from blood. Falkenhagen et al (Artificial Organs (1996) 20:420) described the removal of endotoxin from plasma using polyethyleneimine coated beads. WO 01/23413 describes oligopeptides having a high degree of dispersity which are used to selectively remove endotoxin from blood or plasma. U.S. Pat. No. 5,476,715 describes materials for the removal of endotoxin from a sample, which comprise a porous carrier made from polymers of acrylic acid and methacrylic acid with a particular particle size and spacing. Staubach et al (Transfusion and Apheresis Science (2003) 29: 93-98) describes a device for endotoxin adsorption which is based on immobilized albumin. There are thus a number of available methods which could be used to remove endotoxin from a sample. Any of these methods may be used or adapted for use in accordance with the present invention. The skilled reader would be able to select a suitable method and conditions for its use.

The apparatus or method of the invention will preferably be effective in achieving a significant reduction in circulating blood endotoxin levels. For example, the apparatus or method may lead to a reduction by at least 25%, at least 50%, at least 70%, at least 80%, at least 90%, at least 95%, at least 99% or more in the level of endotoxin in the blood of the individual.

The two aspects of the present invention are also linked. Albumin is capable of binding endotoxin in the blood. Thus, the removal of albumin may also lead to the removal of some endotoxin which is bound to albumin. Furthermore, by increasing the level of normal albumin in the individual, again, albumin in the blood can bind to circulating endotoxin and the levels of free endotoxin in the blood may be decreased. However, the amount of endotoxin reduction achieved in this way is relatively small, so the present invention preferably utilises separate means for (a) removing albumin and (b) reducing endotoxin levels. This effect of albumin removal and/or replacement may supplement other means for reducing endotoxin and may help to "mop up" endotoxin remaining in the blood of the individual.

Based on these findings, the inventors have developed a new method and apparatus for use in the treatment of individuals having liver disease. These comprise a combination of components which act to remove both albumin and endotoxin from the blood of an individual having liver disease.

Particularly, the inventors have developed an apparatus for use in the treatment of an individual having liver disease, the apparatus comprising means for selectively removing albumin from the blood of the individual and means for selectively removing endotoxin from the blood of the individual. Preferably these are two separate means, each directed to achieving one of these effects. The apparatus may also comprise means for supplying new albumin, that does not derive from the individual, to the blood of the individual.

Use of such an apparatus thus results in the removal of albumin from the blood of the individual, a reduction in the level of endotoxin in the blood of the individual and optionally the introduction of new albumin to the blood of the individual. This is therapeutically useful in a variety of ways. Removal of endogenous albumin from the blood of an individual may result in the removal of unwanted toxins bound to the albumin and may also result in the removal of abnormal modified forms of albumin from the blood. Such modified forms often have reduced functional ability. The optional introduction of new albumin can be used to replace the albumin that has been removed with fresh albumin. Preferably the fresh albumin does not comprise toxins bound to the albumin molecules and preferably the fresh albumin is in unmodified form. The addition of fresh albumin to the blood can also be used to supplement endogenous albumin levels where these are reduced as a result of liver disease. Finally, the removal of endotoxin from the blood of an individual having liver disease can help to reduce the level of activation of neutrophils in the blood of the individual. This reduction in neutrophil activation can lead to decreased risk of infection, organ failure and mortality, and can improve the responsiveness of the individual to immunosuppressive therapy and steroid or antibiotic treatment.

The methods and apparatus of the invention thus provide a targeted approach to the treatment of liver disease, addressing multiple factors linked to such disease and benefiting the individual in multiple ways.

In one aspect, therefore, the invention relates to an apparatus for use in the treatment of an individual with liver disease. The apparatus may comprise a number of components, which may be used in combination or separately. An apparatus of the invention will comprise or consist essentially of means for selectively removing albumin from the blood of an individual and means for selectively removing endotoxin from the blood of the individual.

Any means described herein may be used for the removal of albumin or endotoxin. In one aspect, a single component of the apparatus may be used for the removal of both albumin and endotoxin. Typically, such a component of the apparatus will comprise both means for removing albumin and means for removing endotoxin. For example, where albumin and endotoxin are both to be removed by binding to specific ligands, then one or more ligands specific for albumin and one or more ligands specific for endotoxin may be used together in the same component of the apparatus. For example the apparatus may comprise a single container, such as a column or filter bed, which comprises solid support(s) onto which the two ligands are immobilised. The ligands may be immobilised onto different supports or onto the same support. The albumin and endotoxin may thus be removed simultaneously from the blood of the individual.

Alternatively, the apparatus may include separate means for removal of albumin and endotoxin. The apparatus may include more than one means capable of removing albumin and/or more than one means capable of removing albumin.

The apparatus may comprise further components. For example, the apparatus may comprise means for supplying new albumin, i.e. albumin that does not derive from the individual, to the blood. The apparatus may be for use ex vivo. For example, the apparatus may be designed such that blood from the individual passes through it so as to achieve albumin removal and endotoxin removal before returning to the body of the individual.

Two possible apparatuses are illustrated in FIG. 11. It will be clear from the discussion herein and the two apparatuses that are exemplified in FIG. 11 that a number of different components may be used in a variety of combinations in order to achieve the desired effects.

The components of the first illustrated apparatus in FIG. 11 are as follows:
1. Means for trapping albumin. The albumin trap selectively removes albumin from the blood of the patient.
2. Means for carrying out albumin dialysis to remove toxins. For example, the use of a large pore membrane (greater than 50 kDa) to allow albumin exchange permits improved toxin removal by allowing patient albumin to interact with the "cleaning" filters. This also permits the removal of patient albumin as it is exchanged across the filter with the albumin dialysate.
3. Filters to clean albumin.
4. Endotoxin removal component.
5. New albumin infusion.

The components of the second illustrated apparatus in FIG. 11 are as follows:
1. Bacterial lipopolysaccharide trap. This is a means for removal of LPS/endotoxin from the blood of the patient.
2. Means for carrying out albumin dialysis to remove toxins. For example as discussed for the first illustrated apparatus in FIG. 11.
3. Filters to clean albumin.
4. Albumin replacement means. For example, a diffusion gradient for removing the patients albumin and replacing it with fresh albumin.
5. New albumin infusion.

The invention also relates to a method of treating liver disease by using the apparatus of the invention. For example, blood from the individual may be contacted with an apparatus of the invention such that albumin and endotoxin are removed from the blood and albumin that does not derive from the individual may optionally be supplied to the blood. This method may be carried out ex vivo and the blood may be subsequently returned to the individual.

The invention relates to a method of treating an individual having liver disease. The method comprises or consists essentially of the following steps: (a) removing albumin from the blood of the individual; and (b) reducing the level of endotoxin in the blood of the individual. This may be achieved by any method or means as described herein. This method may be carried out ex vivo. Step (a) may be achieved using dialysis. Step (a) may be achieved using a ligand capable of specifically binding albumin. Step (b) may be achieved by directly removing endotoxin from the blood. Step (b) may be achieved using a ligand that specifically binds endotoxin. Step (b) may be achieved by administering to the individual a therapeutically effective amount of an agent capable of reducing the level of endotoxin in the blood. Any combination of step (a) and step (b) methods described herein may be used. Optionally the method further includes the step of introducing albumin that does not derive from the individual into the blood of the individual.

The invention also relates to a method of treating blood extracorporeally by selectively removing albumin and endotoxin from the blood, wherein the blood is from an individual having liver disease. This method may be achieved by any suitable means as described herein and may comprise the additional step of adding to the blood albumin that does not derive from the individual. Blood which has been treated in this way may be returned to the individual for therapeutic purposes, or may be used for another purpose. For example, blood may be treated in this way prior to transfusion into a different individual.

The individual to be treated according to the invention is an individual having liver disease. Liver failure is the final stage of liver disease. Liver failure is divided into types depending on the rapidity of onset. Acute liver failure develops rapidly, but chronic liver failure may take months or years to develop. By definition, liver failure occurs when the liver is so diseased, and functioning so poorly, that encephalopathy is evident. Any progressive liver disease can result in liver failure; examples include: acetaminotophen toxicity, cirrhosis, viral hepatitis, and metastatic cancer of the liver. Other signs of liver disease such as jaundice, ascites, fetor hepaticus, and failure of coagulation indicate that the liver is having trouble performing its normal physiological duties, but it is not termed liver failure until the mental status changes appear.

The prognosis for patients with liver disease is difficult to estimate because the condition has many causes.

Accordingly, the individual to be treated may be an individual whose liver is decompensated or which shows hepatic encephalopathy. The individual's liver may be in the compensated state. The individual may have chronic liver disease. The individual may have liver cirrhosis, for example with or without alcoholic hepatitis. The individual may have acute liver failure. The individual may have hepatic encephalopathy.

The onset of both acute and chronic liver disease may be due to a xenobiotic cause. For example, the individual may have been exposed to a chemical, drug or some other agent which causes liver damage. The individual may have a reaction to an over-the-counter, prescriptive or "recreational" drug which causes liver damage. The individual may have been taking Rezulin™ (troglitazone; Parke-Davis), Serzone™ (nefazodone; Bristol-Myers Squibb) or other drugs thought to cause liver damage. The individual may be one who has had an overdose of a particular drug or exceeded the recommended dosage of a drug capable of causing liver damage. For example, the individual may have taken an overdose of paracetamol. The individual may have been exposed to chemicals which can cause liver damage such as, for example, at their place of work. For example, the individual may have been exposed to such chemicals in an industrial or agricultural context. The individual may have consumed plants which contain compounds which can cause liver damage, in particular this may be the case where the individual is an animal, such as a herbivore. For example, the individual may have consumed a plant containing pyrrolizidine alkaloid such as ragwort. The individual may have been exposed to environmental toxins thought to cause liver disease.

Drug-related liver toxicity comprises more than 50% of all cases with acute liver disease (acute liver failure). Acetaminophen-(also known as paracetamol and N-acetyl-p-aminophenyl) toxicity is the most common cause of acute liver failure in the United States and Great Britain. Long-term moderate to heavy alcohol users who take acetaminophen in therapeutic or modestly excessive doses are at risk of severe hepatic injury and possibly acute liver failure. Alcohol use potentiates the toxic effects of acetaminophen. Idiosyncratic drug toxicity also contributes to acute liver failure. Idiosyncratic drug toxicity is thought to be a hypersensitivity response wherein the individual responds to a drug in a pharmacologically abnormal way. This abnormal response can lead to acute liver failure.

The acute liver failure or chronic liver disease may be caused by infection with a pathogenic organism. For example, the liver disease may be due to viral infection. In particular, the individual may be infected, or have been infected, with a virus which causes hepatitis. The individual may have chronic viral hepatitis. The virus may, for example, be hepatitis B, C or D virus. In some cases, and in particular where the individual has viral hepatitis, the individual may also be infected with HIV-I or II. The individual may have AIDS. It is possible that the individual may have been, or be, infected with other organisms which cause liver disease and in particular those which are present in the liver during some stage of their life cycle. For example, the individual may have, or have had, liver fluke.

The individual may have an inherited disease which causes, or increases the risk of, chronic liver disease. For example, the individual may have one or more of hepatic hemochromatosis, Wilson's disease or α-1-antitrypsin deficiency. The individual may have an inherited disorder which causes some kind of structural or functional abnormality in the liver which increases the likelihood of liver fibrosis. The individual may be genetically predisposed to develop an autoimmune disorder which damages the liver and hence which can contribute to liver fibrosis.

The chronic liver disease may be alcohol-induced. A man or woman to be treated may be, or have been, an alcoholic. He or she may be, or have been, consuming on average 50 or more units of alcohol per week, 60 or more units of alcohol per week, 75 or more units of alcohol per week and even 100 or more units of alcohol per week. The man or woman may be, or have been, consuming on average up to 100 units of alcohol per week, up to 150 units of alcohol per week and even up to 200 units of alcohol per week. The measurement of one unit of alcohol differs from country to country. Here, one unit equals 8 grams of ethanol in accordance with the United Kingdom standard.

The man or woman may have been consuming such levels of alcohol for 5 or more years, 10 or more years, 15 or more years or 20 or more years. The individual may have been consuming such levels of alcohol for up to 10 years, up to 20 years, up to 30 years and even up to 40 years. In cases of alcohol-induced liver cirrhosis the individual may be aged, for example, 25 years or over, 35 years or over, 45 years or over and even over 60 years.

The individual may be male or female. Women may be more susceptible to the adverse effects of alcohol than men. Women can develop alcoholic chronic liver disease in a shorter time frame and from smaller amounts of alcohol than men. There seems to be no single factor to account for increased susceptibility to alcoholic liver damage in females, but the effect of hormones on the metabolism of alcohol may play an important role.

Thus, the individual may be suffering from alcoholic hepatitis. Alcoholic hepatitis may range from a mild hepatitis, with abnormal laboratory tests being the only indication of disease, to severe liver dysfunction with complications such as jaundice (yellow skin caused by bilirubin retention), hepatic encephalopathy, ascites, bleeding esophageal varices, abnormal blood clotting and coma.

The individual may have one or more of a number of other conditions known to result in liver damage such as, for example, primary biliary cirrhosis, autoimmune chronic active hepatitis, and/or schistosomiasis (parasitic infection). The individual may have or have had a bile duct blockage. In some cases, the underlying cause of liver disease may not be known. For example the individual may have been diagnosed as having cryptogenic cirrhosis. Accordingly, the individual may be suspected of having any of the conditions listed herein.

Methods for diagnosing liver disease such as acute liver failure and hepatic encephalopathy are well known in the art and in particular to clinicians and veterinarians in the field. Preferably, the individual will have been diagnosed as having a liver disease and hepatic encephalopathy, for example by a medical or veterinarian professional. The individual may display one or more symptoms associated with liver disease such as one or more of jaundice, ascites, skin changes, fluid retention, nail changes, easy bruising, nose bleeds, oesophageal varices, and in male individuals may have enlargement of breasts. The individual may display exhaustion, fatigue, loss of appetite, nausea, weakness and/or weight loss. The individual may also display one or more symptoms associated with hepatic encephalopathy such as one or more of confusion, disorientation, dementia, stupor, coma, cerebral edema, multiorgan failure (respiratory failure, cardiovascular failure or kidney failure), muscle stiffness/rigidity, seizures or speech impairment. The individual to be treated may or may not be taking other drugs to treat liver disease. The individual to be treated may be at risk of developing hepatic encephalopathy.

The liver disease may have been, or be, confirmed by physical examination including techniques such as ultrasound. Liver biopsies may have been taken to look for build up of fibrosis, necrotic cells, cellular degeneration and/or inflammation and other characteristic features of liver disease. Liver function may have been assessed in the individual to determine whether this is compromised in the individual. The nature and underlying cause of the liver disease may be characterized. Any history of exposure to causative agents of liver disease may be determined.

The individual to be treated may be at risk for hepatic encephalopathic episodes, for example patients who are awaiting liver transplants, surgical and/or portal hypertension patients. A person at risk for hepatic encephalopathic episodes is a person who has not suffered any hepatic encephalopathic episodes or has not suffered any hepatic encephalopathic episode for an extended period of time (about 12 weeks or longer), but has a disorder or medical condition which creates a risk of hepatic encephalopathic episodes. A hepatic encephalopathic episode is a clinical condition characterised by the presence of cerebral dysfunction in patients with liver disease or dysfunction. There is a wide spectrum of mental disturbances in hepatic encephalopathy which range from minimal where the main effects are a reduction in the quality of life, to overt which leads to coma and ultimately death.

The individual on which the method of the invention is practiced may be a liver transplant patient, an individual suffering from reperfusion injury, for example in a graft after liver transplantation or a patient at risk of developing or who has developed multi-organ failure.

Where the level of endotoxin is reduced using an agent to be administered to the individual, the agent may be administered in a variety of dosage forms. Thus, an agent may be administered orally, for example as tablets, troches, lozenges, aqueous or oily suspensions, dispersible powders or granules. The agent may also be administered parenterally, either subcutaneously, intravenously, intramuscularly, intrasternally, transdermally or by infusion techniques. The agent may also be administered in the form of a suppository. A physician will be able to determine the required route of administration for each particular patient.

The formulation of an agent will depend upon factors such as the nature of the exact agent, whether a pharmaceutical or veterinary use is intended, etc. All agent which is to be used to treat liver disease may be formulated for simultaneous, separate or sequential use.

An agent is typically formulated for administration in the present invention with a pharmaceutically acceptable carrier or diluent. The pharmaceutical carrier or diluent may be, for example, an isotonic solution. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, gum arabic, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tabletting, sugar-coating, or film-coating processes.

Liquid dispersions for oral administration may be syrups, emulsions or suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for intravenous administration or infusion may contain as carrier, for example, sterile water or preferably they may be in the form of sterile, aqueous, isotonic saline solutions.

The dose of an agent may be determined according to various parameters, especially according to the substance used; the age, weight and condition of the patient to be treated; the route of administration; and the required regimen. Again, a physician will be able to determine the required route of administration and dosage for any particular patient. A typical daily dose is from about 0.1 to 50 mg per kg of body weight, according to the activity of the specific inhibitor, the age, weight and conditions of the individual to be treated, the type and severity of the degeneration and the frequency and route of administration. Preferably, daily dosage levels are from 5 mg to 2 g.

All publications and patent applications mentioned in this specification are indicative of the level of those skilled in the art to which this invention pertains.

All publications and patent applications are herein incorporated by reference to the same extent as if each individual publication or patent application was specifically and individually to be incorporated by reference.

Although the foregoing invention has been described in some detail by way of illustration and example for purposes of understanding, it will be clear to those skilled in the art that certain changes and modifications may be practiced within the scope of the appended claims.

The following Examples illustrate the invention:

EXAMPLES

Example 1

Albumin Studies in Patients with Cirrhosis

We aimed to undertake a qualitative assessment of albumin functionality in increasing severity of liver disease, using a spin label and electron paramagnetic resonance spectroscopy. A spin label for albumin, 16-doxil stearic acid (SL), was added to plasma samples from healthy volunteers (control, n=5), stable well compensated cirrhotic subjects (cirrhotic, n=5) and patients with acute or chronic liver failure (ACLF, n=10). 5 patients were treated with molecular adsorbents recirculating system (MARS, 4 sessions) and 5 with standard medical therapy. Measurements were made before and after 7 days of MARS. Aliquots of ethanol were then added to the labelled plasma samples and the EPR spectra recorded following each addition. Analysis of the recorded spectra provided information on albumin conformation and binding properties. For each parameter measured, the patient's albumin was found to have lower functional ability than that from healthy volunteer controls. In liver failure a further decrease in function was found. No change in the albumin status was observed following MARS therapy.

| | Healthy controls | Stable Cirrhotic | ACLF |
|---|---|---|---|
| Molecular flexibility ($D_R$) [≧1] | 4.706** | 1.194 | −1.613 |
| Fatty acid binding ($K_B$) [≧8.5] | 17.34* | 4.888 | 1.375 |
| Conformational stability ($L_2$) [2.9] | 2.939 | 2.335†† | 1.301 |
| Transport quality (RTQ) [%] | 84.60* | 49.20† | 10.83 |
| Transport efficiency (RTE) [%] | 87.00* | 49.20 | 42.33 |
| Detoxification ability (DTE) [%] | 130.3* | 49.80† | 4.000 |

* $p < 0.05$,
** $p < 0.01$ vs stable cirrhotic subjects,
† $p < 0.05$,
†† $p < 0.01$ vs AoCLF day 0.
Values in [ ] indicate previously established normal healthy reference values.

The results from this study clearly indicated that the patient's albumin was severely compromised in structure and function, which worsens in liver failure. These patients are typically associated with reduced plasma albumin concentrations, and this combination of factors will result in extremely low functional capacity. Though MARS has been shown to remove albumin bound toxins, it fails to address the underlying problem of poor quality patient albumin.

In this same group of patients we have also examined plasma samples for the presence of ischaemia modified albumin (IMA). IMA is determined by examining the ability of albumin to bind metal atoms. In functional albumin the metal binding function is high, but following oxidative stress (as may be encountered during ischaemia and reperfusion) the protein structure is damaged and the ability to bind metals is diminished.

Figure 1:
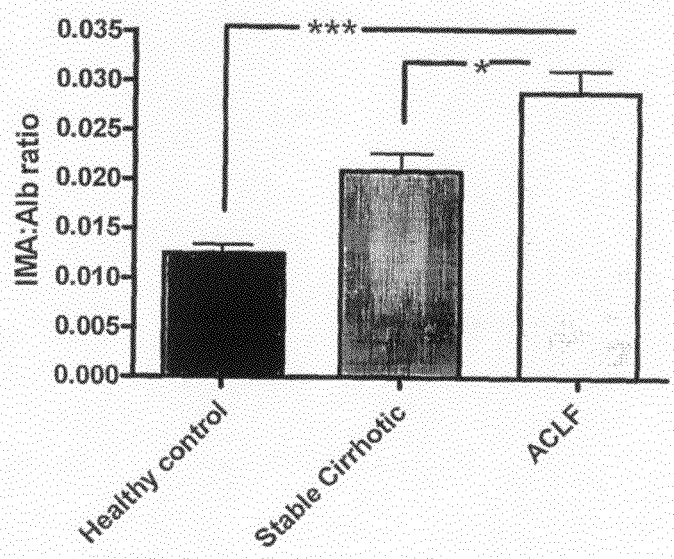
FIG. 1: Increasing ischaemia modified albumin (IMA) levels are found to be associated with severity of liver disease. Values are expressed as IAM absorbance units per g/L plasma albumin, (mean+ or −SEM). *=p<0.05, ***=p<0.001.

In our group of patients we found that the amount of IMA (relative to the plasma albumin content, see FIG. 1) was significantly increased ($p<0.001$) in patients with liver disease compared with healthy control subjects. A significant increase was also found between stable cirrhotic and ACLF subjects, again indicating that further albumin damage is associated with increasing severity of disease.

Though the exact protein modification that results during IMA formation is still the subject of investigation, the region has been identified as being within 20 amino acid residues of the N-terminus. This is of interest as it is distinctly different from the identified fatty acid binding sites examined using the EPR labelling technique described above, and indicates that there are a number of post-translational modification processes associated with severe liver disease.

Example 2

Neutrophil Function Studies

The aims of our study were to systematically examine the essential neutrophil functions, (oxidative burst and phagocytosis) in patients with alcoholic hepatitis and examine its relationship with infection rates, organ failure and survival. In ex vivo studies we investigated whether the defect in neutrophil function was due to a humoral factor and whether endotoxin removal from plasma would restore the patient's neutrophil function.

For experiments with cells, whole blood or isolated neutrophils (and patient plasma) were used to perform the Phagoburst® or the Phagotest® assays (Orpegen Pharma, Heidelberg, Germany). For all experiments strict precautions were taken to avoid endotoxin contamination by working aseptically and using endotoxin-free equipment.

Methods

Patient Selection

All patients or their relatives gave written informed consent and the study was approved by the local ethics committee. Patients admitted with evidence of alcoholic cirrhosis were screened for this study, at the time of a clinically indicated transjugular liver biopsy. The patients were included if they were admitted with acute decompensation of alcoholic cirrhosis manifested by increasing jaundice, ascites or hepatic encephalopathy grade 1 or 2 and there was no if there was microbiological evidence (routine cultures of urine, blood, sputum and ascites) of infection. Patients were excluded if they were <18 or >75 years, had evidence of: organ failure (inotrope requirement, renal failure–creatinine>150, hepatic encephalopathy grade 3 or 4, need for mechanical ventilation, severe cardiac dysfunction), hyponatremia, hepatic/extra-hepatic malignancy, within 3 days of gastrointestinal bleeding or if they received any immunomodulatory therapy prior to entry in the study.

Study Design

Following correction of any associated electrolyte disturbance or hypovolemia, blood samples were collected and used for routine biochemistry, neutrophil function, cytokine profile and thiobarbituric acid (T-BARS/modified MDA) detection. Peripheral venous blood was aseptically collected into pyrogen free tubes (BD Vacutainer Lithium-Heparin, 60U per tube, Beckton and Dickinson, Plymouth, UK)) from patients and healthy volunteers. For experiments with cells, blood was kept at room temperature, for harvesting plasma, blood was placed on ice immediately. After centrifugation the plasma was aliquoted under pyrogen-free conditions into endotoxin-free cryotubes (Corning Inc., Corning, N.Y.) and stored at −80° C. until further analysis. 100 µL of whole blood or 50 µL of isolated neutrophils and 50 µL of plasma were used to perform the Phagoburst® or the Phagotest®. For all experiments strict precautions were taken to avoid endotoxin contamination by working aseptically and using endotoxin-free equipment. Bilirubin, albumin, liver function tests, coagulation parameter, full blood count, and C-reactive protein (CRP) were routinely assessed. Maddrey's discriminant function and Pugh score were calculated. The patients were followed prospectively over a period of 90 days. The occurrence of organ dysfunction and mortality were recorded. Screening blood cultures were performed regularly, and our unit policy was to use prophylactic antibiotics at the time of presentation in most patients.

Neutrophils

Neutrophils were either investigated in a whole blood assay (as described below) or after isolation by a one-step gradient centrifugation (as indicated in the result section, see appendix).

Figure 2:
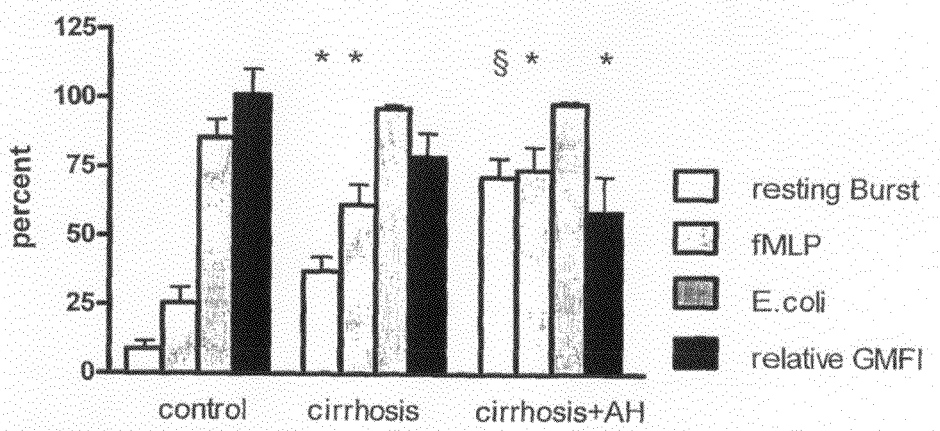
FIG. 2: (A) Resting oxidative burst (%) in controls, patients with cirrhosis alone and patients with cirrhosis+AH, (13) difference between resting oxidative burst and oxidative burst after ex vivo stimulation with $E.\ coli$ in controls, patients with cirrhosis alone and patients with cirrhosis+AH, (C) geometric mean of fluorescence intensity (GMFI) as a measure of the number of bacteria (FITC-labelled $E.\ coli$) engulfed by one neutrophil in controls, patients with cirrhosis alone and patients with cirrhosis+AH. Statistical significant differences are indicated by superscripts. 1=significant vs. control. 2=significant vs. cirrhosis.

Neutrophil activation (oxidative burst) and Phagocytosis: The Phagoburst® kit (Orpegen Pharma, Heidelberg, Germany) was used to determine the percentage of neutrophils that produce reactive oxidants by stimulation with opsonized E. coli bacteria or without any stimulus according to the manufacturers instructions. The Phagotest® (Orpegen Pharma, Heidelberg, Germany) was used to measure the overall percentage of neutrophils showing phagocytosis and the individual cellular phagocytotic activity using FITC-labelled opsonized E. coli bacteria (see appendix). Neutrophils were gated on forward and side scatter (FIG. 2) characteristics and subsequently the percentage of CD16 positive cells—FITC positive cells, corresponding to the percentage of neutrophils undergoing phagocytosis and the geometric mean of fluorescence intensity (GMFI), corresponding to the number of bacteria engulfed by one cell, was analyzed. To avoid variability due to batch-to-batch difference of bacteria, results were normalized to the mean of at least 3 healthy control samples for each new batch of bacteria used. Samples were analyzed in triplicate or duplicate.

Incubation with Endotoxin Endotoxin (E. coli 0111:B4 Lot 085K4068, Sigma Aldrich, St. Louis, Mo., USA) was prepared as a stock solution of 1 mg/ml and freshly diluted with PBS to the concentrations indicated. Whole blood was incubated for 1 h with the respective endotoxin concentration at 37° C. in a water bath before Phagotest® or Bursttest® were performed.

Endotoxin Removal from Patient's Columns

Using Detoxigel: Detoxi-Gel® Affinity-pack prepacked columns (Pierce Bioteclnology, Rockford, Ill.) containing an endotoxin removal gel consisting of immobilised polymixin B that binds to the lipid A portion of bacterial lipopolysaccharide were used to remove endotoxin from plasma samples. 100 µL of this endotoxin-free, diluted plasma sample were incubated with 50 µL of cell suspension and Bursttest® or Phagotest® was performed as indicated. (see appendix).

Using CD14 Antibody: 100 µL of plasma and 50 µl of PBS were incubated with 5 µL of an anti-human CD14 antibody (Clone 11D18, Immuntools, Friesoythe, Germany) (known to neutralise LPS) for 60 minutes before performing the Phagotest® or the Bursttest®.

Cytokines

Plasma TNFα, sTNFαR1, sTNFαR2, IL-6 and IL-8 were determined using commercially available sets (BioSource International, Nivelles, Belgium).

Malondialdehyde and Prostaglandin F2α

Malondialdehyde (MDA) was determined using a modified thiobarbituric acid reactive substances assay as known in the art. Free 8-Isoprostane F2alpha was assayed with a commercial EIA kit (Cayman Chemical, Ann Arbor, Mich.).

Statistics

For comparison of two groups Chi-Square test, t-test or Mann-Whitney test were used as appropriate, for comparison of more than two groups ANOVA test with Turkey's (equal variances) or Dunnett C (no equal variances) post hoc analysis for data sets was used as appropriate, To assess diagnostic accuracy, receiver operating characteristic (ROC) curves were constructed and areas under the curve (AUROC) were calculated. Differences in survival were analysed by the log rank test. Pearson's correlation coefficient was used to assess relationship between variables. Results are given as mean±SEM. A p<0.05 was considered as significant.

Results

Patient Characteristics

Of the 72 patients screened, 63 patients were included. Patients were classified histologically into those having significant inflammation, using a modified NASH scoring system (cirrhosis+AH) as compared to cirrhosis alone. Patients with cirrhosis+AH (n=23) were more severely ill as evidenced by a higher MELD and Pugh score (p<0.001) as compared to patients with cirrhosis alone (n=40). Patients with cirrhosis+AH also had significantly higher CRP (p<0.005), white blood cells (p<0.001), bilirubin (p<0.001) and prothrombin time (p<0.001). Patients had higher levels of TNFα, IL6, IL8, sTNFαR1, sTNFαR2, MDA and prostaglandin F2α than controls. Patients with cirrhosis+AH had significantly higher levels of IL6, IL8 and sTNFαR2, but no statistically significant changes were noted for TNFα, sTNFαR1 and oxidative stress. No correlation with disease severity was found. For the ex vivo experiments blood or plasma from 16 of these 63 patients was used. The baseline clinical data for these 63 patients were not significantly different from the whole cohort. Table 1 shows the baseline characteristics for all patients and for the subgroups having high and low resting bust (see below).

Oxidative Burst and Phagocytosis in Patients with Alcoholic Cirrhosis

In un-stimulated patient neutrophils, neutrophil oxidative burst was increased when compared with controls. Neutrophils from patients with alcoholic cirrhosis overall had a 5.6 times higher resting oxidative burst (p<0.001) than healthy controls. Neutrophils from patients with cirrhosis+AH had significantly higher resting oxidative burst compared to patients with cirrhosis alone (p<0.001) or controls (p<0.001, FIG. 2A). Stimulation with fMLP, indicating priming, caused a significant higher oxidative burst reaction in patients with cirrhosis (p=0.01) and cirrhosis+AH (p=0.001) as compared to controls whereas there was no difference in response to PMA between the groups. The difference between resting burst and fMLP response was significantly lower in patients with cirrhosis+AH (1.8±4.7) than in patients in cirrhosis (22.4±6.9, p=0.02), showing that addition of fMLP in patients with cirrhosis+AH is not able to enhance function of the cells any more. Furthermore, following stimulation with E. coli, the relative increase in oxidative burst from resting levels was significantly diminished in cirrhosis+AH patients compared with cirrhosis alone (p=0.001) or controls (p<0.001, FIG. 2B).

Phagocytotic capacity was measured by the geometric mean of fluorescence intensity (GMFI), which indicates the number of bacteria engulfed by one cell. Patients with cirrhosis+AH engulfed significantly less bacteria than controls (p=0.031, FIG. 2C). The percentage of cells engulfing at least one bacterium did not differ between the groups.

Figure 3:
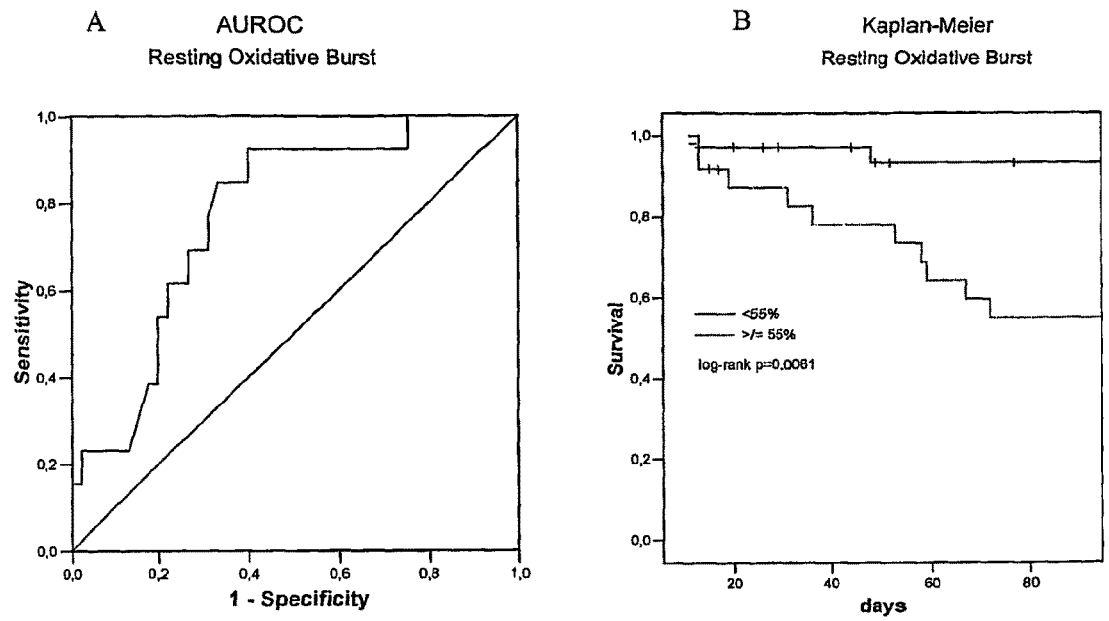
FIG. 3: (A) Area under the receiver operating curve to determine the predictive utility of measurement of oxidative burst in determining survival. A cutoff of resting burst<55% had a sensitivity of 75% and a specificity of 64% for predicting death. (13) Kaplan Meier survival curve and log-rank analysis for patients stratified for high (>/=55%) or low (<55%) resting oxidative burst.

Association of Resting Oxidative Burst and Phagocytosis with Infection, Organ Failure and Survival Seventeen (26%) developed organ failure and 13 (21% of all studied patients) died during index hospital admission. The most common organ failure encountered was renal, noted in 15 of the patients with organ failure (88%), with 4 patients developing this as part of multi-organ failure with requirement for ventilation and circulatory support. By 90 days, 14 (22%) patients had died, 47 were alive and 2 were lost to follow-up. Resting oxidative burst was found to be predictive of 90-day survival (AUROC 0.77, p=0.003, FIG. 3A) and organ failure (AUROC 0.76, p<0.001). A cutoff of resting burst<55% had a sensitivity of 77% and a specificity of 69% for predicting death. Patients with a resting oxidative burst<55% survive significantly better than those with a resting burst>/=55% (p<0.005, FIG. 3B). Phagocytic function was also predictive of survival (AUROC 0.80, p=0.02, FIG. 4A) and organ failure (AUROC 0.91, p<0.0001). A GMFI of lower than 42% of normal within the studied patient population had a sensitivity of 86% and a specificity of 70% to predict mortality (FIG. 4B).

In 42 (66%) patients infection was clinically suspected during the course of the hospital admission although none of the patients included had a proven infection at the time the neutrophil function was assessed. These data should be considered in context since our protocol for management, necessitates the use of broad spectrum antibiotics as soon as an infection is suspected. In 26 of these patients (62%), culture positive infection was verified. In 13, more than one organism was found. Patients with a high resting burst (>55%) were more likely to develop culture positive infections (57% versus 27%, chi-square p=0.01), earlier during hospital stay (8 vs 23 days, p=0.04) and with more than one organism (n=10; n=3 in patients with low resting burst). Patients with cirrhosis+AH were more likely to develop culture positive infections (65% versus 28%, p=0.004). Those who developed culture positive infections, were more likely to develop organ failure (p=0.001) and to die (p=0.002). 67% of patients with a GMFI below 42% developed culture positive infection, whereas only 21% of patients with a GMFI above 42% (p=0.007). Patients with low GMFI developed infections earlier during their hospital stay (9 vs 47 days, p=0.03)

Effect of Patients Plasma and Normal Plasma on Neutrophils Oxidative Burst

Plasma from patients with a high resting burst (>55%; n=6) induced a high resting burst in normal neutrophils (p=0.005) whereas plasma of patients with a low resting burst (<55%; n=6) failed to do so (FIG. 5). The burst-inducing effect was detectable immediately after mixing plasma and cells but could also be shown after up to one hour of incubation (results not shown). This result indicated that there is a transmissible factor present in patient's plasma which causes neutrophils activation.

When isolated neutrophils of patients with high resting burst in the whole blood assay were incubated with normal plasma, the resting burst decreased significantly as compared to isolated neutrophils incubated with the patients own plasma (p=0.02; FIG. 6). These experiments suggested that the removal of a factor present in plasma was able to reduce the high resting burst in patients' cells, Effect of Patients' Plasma and Normal Plasma on Phagocytosis Normal neutrophils incubated with plasma from patients with a low resting burst did not differ from control, whereas normal neutrophils incubated with plasma from patients with high resting burst showed a 22% decrease in GMFI (p=0.03, n=6). Patients neutrophils incubated for 60 minutes with normal plasma showed a 22% increase (p=0.03, n=6) in phagocytosis as compared to patients neutrophils incubated with their own plasma. These results indicate that impairment of phagocytic function may be due to a serum factor that is transmissible and reversible.

Effect of Endotoxin on Oxidative Burst and Phagocytosis

Blood from five healthy volunteers was incubated with rising concentrations of endotoxin. There was a dose dependent increase in resting burst (p<0.0001, one way ANOVA with Turkey post hoc analysis; FIG. 7). By incubation of patient's neutrophils with endotoxin, the relative GMFI was reduced by 20% (n=8, p=0.02, FIG. 8). These results indicate that endotoxin activates normal neutrophils in a dose-dependent manner thereby mimicking the effect seen by incubation with patients' plasma.

Effect of Removing Endotoxin from Patients Plasma a. Using Detoxi-Gel columns: Plasma from patients shown to have a high resting burst in the whole blood assay was able to induce a high resting burst in normal neutrophils. Endotoxin free plasma (obtained from passage through the columns) did not induce a high resting burst in normal neutrophils (p<0.001, n=9). Plasma from patients with low resting burst (p=0.91, n=4) and normal plasma (p=0.25, n=3) did not change resting burst (FIG. 9). Endotoxin removal from the plasma of patients with a high resting burst (n=11) increased GMFI by 31% (p=0.03) as compared to cells incubated with untreated plasma. Plasma from patients with low resting burst (p=0.16, n=8) and normal plasma (p=0.85, n=5) that was passed over the column did cause any changes in GMFI (FIG. 11). This set of experiments shows that endotoxin removal by polymixin B reverses the burst-inducing and phagocytosis-decreasing effect of patients' plasma.

b. Using LPS-neutralising antibodies: Incubation with a LPS neutralising anti-human CD14 antibody prevented the induction of high burst in normal cells by plasma from patients with a high burst (p<0.001, n=7). Incubation of plasma from patients with low burst (p=0.733, n=8) or normal plasma (p=0.25, n=3) with the antibody did not change burst (FIG. 9). Incubation of plasma from patients with a high burst with a LPS neutralising anti-human CD14 antibody increases GMFI by 20% (p=0.04, n=11) whereas this antibody does not cause any changes in GMFI when plasma from patients with low burst (p=0.17, n=8) or normal plasma (p=0.78, n=3) was used (FIG. 10). This finding underpins the observation that endotoxin may be responsible for the induction of high resting burst in neutrophils.

TABLE 1

|  | all (n = 63) | low resting burst (n = 35) | high resting burst (n = 28) |
|---|---|---|---|
| Death (%) | 22 | 9 | 42 |
| Organ failure (%) | 26 | 12 | 43 |
| Age (years) | 50.3 ± 1.3 | 52.4 ± 2.0 | 47.8 ± 1.6 |
| Liver function | | | |
| Bilirubin (mmol/L) | 151.2 ± 20.9 | 104.8 ± 21.8 | 199.8 ± 34.8[1] |
| PT (sec) | 15.3 ± 0.61 | 13.5 ± 0.5 | 16.8 ± 0.9[1] |
| Albumin (g/L) | 29.8 ± 1.1 | 32.7 ± 1.3 | 28.8 ± 1.3[1] |
| Maddrey's DF (n = 23 with AH) | 43.4 ± 6.8 | 40.0 ± 9.5 | 44.6 ± 8.0 |
| Pugh score | 9.3 ± 0.4 | 8.3 ± 0.4 | 10.2 ± 0.5[1] |
| MELD | 15.6 ± 1.8 | 12.2 ± 2.0 | 19.1 ± 3.5 |
| Priming (response to fMLP) | 57.5 ± 5.1 | 47.5 ± 7.9[2] | 89.1 ± 3.2[1,2] |
| Cytokine/Inflammation | | | |
| TNFα (pg/mL) | 19.6 ± 6.5 | 18.3 ± 6.9 | 22.3 ± 14.6 |
| IL-6 (pg/mL) | 49.4 ± 14.9 | 21.9 ± 7.9 | 106.1 ± 39.6 |
| IL-8 (pg/mL) | 180.5 ± 56.9 | 101.8 ± 55.8 | 337.9 ± 122.8 |
| Oxidative Stress | | | |
| MDA (µM/L) | 3.2 ± 0.5 | 3.2 ± 0.58 | 3.0 ± 0.7 |
| Prostaglandin F2α (pg/mL) | 346.8 ± 49.6 | 296.9 ± 43.8 | 394.7 ± 81.2 |

[1]significant versus low burst
[2]significant versus control

TABLE 2

|  | Child C (n = 27) | Child B (n = 26) | Child A (n = 10) | control (n = 13) |
|---|---|---|---|---|
| resting burst % | 67.0 ± 6.5[1,2,3] | 38.2 ± 7.2[1,3] | 36.0 ± 9.0[1] | 8.9 ± 2.7 |
| burst after stimulation - resting burst % | 32.4 ± 6.8[1,2,3] | 57.5 ± 7.0[1,3] | 60.4 ± 8.7[1] | 76.8 ± 7.7 |
| phagocytosis % | 105.9 ± 2.8 | 110.18 ± 3.3 | 107 ± 5.5 | 99.4 ± 7.5 |
| GMFI % | 50.7 ± 9.5[1] | 87.1 ± 13.6 | 104.6 ± 17.1 | 101.0 ± 9.2 |

[1] $p < 0.05$ versus control
[2] $p < 0.05$ versus Child B
[3] $p < 0.05$ versus Child A TABLE OF INFECTIONS
Documented culture positive infections in patients studied

| high burst | | | | low burst | | | | |
|---|---|---|---|---|---|---|---|---|
| | first organism | | second organism | | | first organism | | second organism |
| patient | day | organism | day | organism | patient | day | organism | day | organism |
| 1 | 4 | EC | 29 | MRSA | 2 | 16 | EC | | |
| 4 | 14 | EC | 19 | CNS | 14 | 23 | E. coli | | |
| 5 | 9 | CNS | 34 | EC | 17 | 9 | MRSA | | |
| 7 | 4 | EC | 10 | CNS | 23 | 15 | St. aureus | | |
| 12 | 2 | C. albicans | | | 33 | 15 | Propionibacterium | 34 | CNS |
| 13 | 10 | St. aureus | | | | | | | |
| 15 | 8 | CNS | | | | | | | |
| 20 | 5 | EC | 5 | CNS | | | | | |
| 35 | 6 | EC | | | | | | | |
| 36 | 4 | CNS | 4 | EC | | | | | |
| 45 | 2 | CNS | 3 | CNS | | | | | |
| 48 | 20 | E. coli | | | | | | | |
| 61 | 6 | C. albicans | | | | | | | |
| 62 | 7 | C. albicans | 9 | EC | | | | | |

EC: *Enterococcus*, MRSA: methicillin-resistant *Staphylococcus aureus*, CNS: coagulase-negative *Staphylococcus*, St.: *Staphylococcus*, Str.: *Streptococcus*, C.: *Candidia*

Methodology
Neutrophil Activation (Oxidative Burst) and Phagocytosis

The Phagoburst® kit (Orpegen Pharma, Heidelberg, Germany) was used to determine the percentage of neutrophils that produce reactive oxidants by stimulation with opsonized *E. coli* bacteria or without any stimulus according to the manufacturers instructions. In brief, 100 µl of heparinized whole blood or isolated neutrophils (as indicated) were incubated for 20 minutes with 20 µl of the bacteria, N-formylmethionyl-leucyl-pehnylalanine (fMLP), phorbol 12-myristate 13-acetate (PMA) or without stimulus at 37° C. Formation of the reactive oxidants during the oxidative burst was monitored by the addition and oxidation of dihydrorhodamine 123. To identify neutrophils, cells were stained with anti-CD16-PE antibody (IOTest®, Beckman Coulter) and analysed by fluorescence activated cell sorting. (FACS), (Becton Dickinson FACScan, San Jose, Calif.) using Cellquest™ software. Neutrophils were gated on forward and side scatter characteristics and subsequently the percentage of CD16 positive cells producing reactive oxygen metabolites determined by green fluorescence (FL-1) measurement. Samples were analyzed in triplicate or duplicate. The interassay coefficient of variation (CV) for resting burst was 5.4%, for stimulated burst 4.2%, the intraassay CV for resting burst was 4.7%, for stimulated burst 2.4%.

Neutrophil Phagocytosis

The Phagotes® (Orpegen Pharma, Heidelberg, Germany) was used to measure the overall percentage of neutrophils showing phagocytosis and the individual cellular phagocytotic activity using FITC-labelled opsonized *E. coli* bacteria. 100 µl of whole blood or isolated neutrophils (as indicated below) were incubated with 20 µl of bacteria at 37° C. for 20 min while a negative control sample remained on ice. To identify neutrophils, cells were stained with anti-CD-16-PE antibody (IOTest®, Beckman Coulter) Neutrophils were gated on forward and side scatter (FIG. 2A) characteristics and subsequently the percentage of CD16 positive cells—FITC positive cells, corresponding to the percentage of neutrophils undergoing phagocytosis and the geometric mean of fluorescence intensity (GMFI), corresponding to the number of bacteria engulfed by one cell, was analyzed (FIG. 1B, D, F). To avoid misinterpretation of results due to batch-to-batch variability of bacteria, results are normalized to the mean of at least 3 healthy control samples for each new batch of bacteria used. Samples were analyzed in triplicate of duplicate. The interassay CV for percentage of phagocytosis was 6.8%, for GMFI 10.1% the respective intraassay CV for percentage of phagocytosis was 4.1%, and 1.6% for GMFI.

Neutrophil Isolation 4 ml of whole blood were layered over 5 ml of Polymorphoprep (Axis-Shield, Oslo, Norway) and spun for 30 min at 400 g, at room temperature. Neutrophils were harvested from the second interface and washed with PBS ((Sigma Aldrich, St. Louis, Mo., USA). Neutrophils are counted in a Thoma-hemocytometer and resuspended in PBS at a density of $5 \times 10^6$ cell in 50 μL. 50 μL of cell suspension and 50 μL of plasma were used for one assay. Viability was tested by Trypan Blue exclusion and was over 98%.

Endotoxin Removal Columns

Detoxi-Gel Affinity-pack prepacked columns (Pierce Biotechnology, Rockford, Ill.) containing an endotoxin removal gel consisting of immobilised polymixin B that binds to the lipid A portion of bacterial lipopolysaccharide were used to remove endotoxin from plasma samples. The columns were regenerated with 1% sodium deoxycholate (Sigma Aldrich, St. Louis, Mo., USA), washed with sterile water and equilibrated with sterile sodium chloride 0.9% supplemented with 50 IU/ml of heparin (Multipharm, Waxham, UK) at room temperature. Plasma samples are diluted 1:1 with PBS and applied on the column and after discarding the void the sample was collected in a pyrogen free sample tube. 150 μL of this endotoxin-free, diluted plasma sample were incubated with 50 μL of cell suspension and Bursttest® or Phagotest® was performed as indicated.

Cytokines

TNFα, sTNFαR1, sTNFαR2, IL-6 and IL-8 were determined from ethylene-diamine-tetraacetate anticoagulated plasma samples using commercially available sets (BioSource International, Nivelles, Belgium) following the manufacturer's instructions. The lower limit for the detection of the cytokines was 3 pg/mL. The intra-assay coefficient of variation was 5.4% to 6.4%. IL-6 and IL-8 were undetectable in controls.

Example 3

Effects of Albumin Administration and Bacterial Endotoxin Sequestration in a Rodent Model of Decompensated Cirrhosis The purpose of this study was to test whether albumin and/or endotoxin removal would be beneficial in a rodent model of decompensated cirrhosis. In this model, the additional insult secondary to the cirrhosis is instigated via the infusion of bacterial endotoxin (lipopolysaccharide, LPS) which is commonly used to simulate the effects of infection.

Methods.

All studies were conducted according to Home Office guidelines under the Animals in Scientific Procedures Act 1986. Male Sprague-Dawley rats (230-280 g, Charles Rivers Ltd.) were given free access to normal rodent chow and water, with a light dark cycle of 12 hours, 19-23° C., and humidity of approximately 50%.

Bile duct ligation (BDL) was achieved by making a midline abdominal incision under anaesthesia. In the BDL group, the common bile duct was isolated, triply ligated with 3-0 silk, and sectioned between the ligatures. After BDL, all animals continued to gain weight and were comparable with naive controls. The overall mortality was less than 10% and occurred within 36 hours of the operation.

Between 24-26 days post surgery the animals were anaesthetised and indwelling cannulae were inserted into the left carotid artery and right jugular vein. The arterial line was used for continuous blood pressure monitoring (Biopac Systems, Goleta, Calif. USA) and blood sample collection, and the venous line for continuous infusion of fluids.

All BDL animals received an intra-venous infusion of LPS (1 mg/Kg, *Klebsiella pnuemoniae*, Sigma, Poole. UK.) over 20 minutes followed by a continuous infusion (10 mls/Kg/hour) of: i) Saline; ii) Albumin (1.5 g/Kg, Zenalb, BPL, Elstree. UK) in saline; iii) Polymixin B (2 mg/Kg, Sigma, Poole. UK); or iv) albumin plus polymixin B (as above): to a total experimental time of 3 hours post surgery. Arterial samples were collected at 0, 1, 2 and 3 hours for analysis of neutrophil function.

The animals were killed by exsanguinations under anaesthesia, with the blood collected for analysis. All studies were performed on liver tissue at 25 to 28 days post BDL, and 4 animals were used in the final analysis in each group.

At the end of the experiment blood was collected into ice-cold sterile tubes (BD Vacutainer system, Becton Dickenson. UK), and held on ice before centrifuging (3000 rpm, 4° C., 10 minutes) to separate the plasma which was then stored at −80° C. prior to analyses.

Plasma was analysed for endotoxin content using the commercially available Endosafe system (Charles Rivers Laboratories, Cedex, France) measured using a Tecan Sunrise 96 well plate reader (Tecan, Austria) according to manufacturer's instructions (see, for example, Stadlbauer et al J. Hepatol 2007; 47: 726-727). Plasma was also measured for albumin content, ALT, and urea, using a Cobas Integra 400 laboratory analyser (Roche Diagnostics, Sussex. UK).

Neutrophil function was measured using a Phagoburst assay kit (Orpegen, Heidelberg, Germany) using a FACS-canto flowcytometer (Becton Dickenson, UK) according to manufacturer's instructions (see, for Example, Mookerjee et al Hepatology 2007; 46: 831-840).

Statistical analyses were conducted using the Graphpad Prism software package (Graphpad, Ca, USA) using the methods indicated.

Results.

It can be seen in FIG. 12 that endotoxin was readily detectible in the plasma of saline treated animals after 3 hours. In the groups given polymixin B, either alone or in combination with albumin, the endotoxin level was found to be below the detection limit of the assay. A small amount was found present in the albumin-only treated group, though this was still a small fraction compared to the saline treated animals ($p<0.001$). Though it is known that albumin has the ability to bind albumin, it was not found to be as effective at the administered dose as polymixin.

BDL animals are known to have significantly reduced plasma albumin concentrations resulting from the ongoing liver injury. Albumin administration was found to significantly increase the measured plasma albumin levels ($p<0.05$ vs saline) by approximately 25%. Though this was still found to be significantly less than samples collected from naïve healthy animals ($p<0.01$, FIG. 13A).

Though it would be expected that BDL animals would have increased transaminase levels (ALT, FIG. 13B) it was interesting to note that each of the treatment groups were found to have lower ALT scores. Though these differences were not found to be significant due to intra-group variation, it would appear that endotoxin exacerbates the underlying liver condition its removal is beneficial for the liver.

Figure 13C:
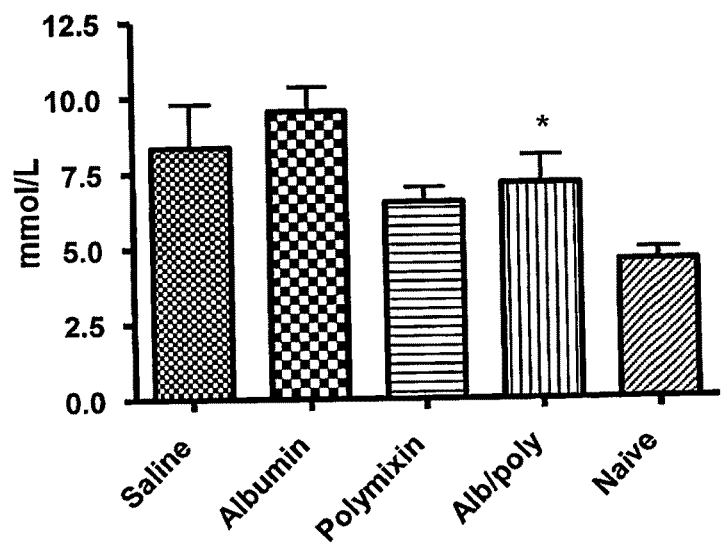

Urea levels were elevated in all groups compared with naive healthy animals, but were found to be significantly lower in the albumin/polymixin group compared with the albumin only group ($p<0.05$, FIG. 13C). Reduced levels were also observed in the polymixin only group.

FIG. 14 shows the measured mean arterial pressure data collected throughout the study period. It can be seen that the saline only group maintains the initial pressure for the first 90 minutes, after which a progressive deterioration is observed. Both the albumin and albumin/polymixin groups maintain blood pressure throughout the whole study period, with the albumin/polymixin animals showing an increase in pressure at 3 hours. It should be noted that all of the BDL animals are considered to be hypotensive at the start of the study as the normal MAP for an anaesthetised rat should be circa. 120 mmHg.

In FIG. 15 it can be seen that there is a progressive improvement in the ability of the neutrophils to respond to pathogenic bacteria in both the albumin and albumin/polymixin group, with apparently better response with the combination therapy. No change is evident in the saline treated animals. The polymixin B only group has not been included in this figure due to clotting irregularities preventing a representative sample size being presented. Measurements of spontaneous neutrophil activity were also made, though no differences between groups were observed in these samples.

Discussion

It is evident that the administration of albumin to an established rat model of cirrhosis is beneficial in preventing an acute deterioration following exposure to bacterial toxins. Furthermore, these effects are improved by the synergistic addition of an agent to bind and remove endotoxin.

In FIG. 12, the removal of measurable endotoxin from the system was only achieved in the groups treated with polymixin B, though the albumin only group did achieve a substantive reduction. It may be that increasing the albumin dosage further would have further reduced the plasma endotoxin level, however this dose was chosen to reflect a typical amount given to hospital inpatients and was not targeted at LPS binding specifically. It is not clear how much free endotoxin in the system is required to exert a negative physiological response.

Though, as expected, the administration of albumin caused a significant increase in the measured plasma levels, these were still found to be lower than in healthy animals. In this study we aimed to provide a typical therapeutic daily dose of albumin, though hospital patients would be expected to receive this treatment on successive days. It is likely that the existing albumin in these animals has been damaged by the disease process and that the provision of new, 'healthy' albumin has a substantial metabolic benefit to the animal.

It was expected to find increased ALT levels in all of the BDL animals due to the ongoing liver damage, however it appear as though the administration of endotoxin causes a further deterioration in the state of the liver which was ameliorated in the treatment groups. Though these differences were not found to be significant due to intra-group variation, it would appear that treatment with polymixin B is most effective in preventing further liver damage.

Urea levels are a reflection of both the synthetic processes resulting from protein breakdown and the ability of the kidneys to excrete waste products from the body. It is interesting to note that a significant difference was observed between the albumin only and albumin/polymixin treated groups. The albumin treated animals showed a slight increase in urea levels compared with the saline group, which may reflect the amount of protein being administered. Interestingly, the animals receiving the combination treatment had significantly lower plasma urea levels. This reduction in plasma urea may be related to the improved mean arterial pressure levels observed in these animals (FIG. 15). As stated above, all of these BDL animals were found to be hypotensive which is known to cause a reduction in renal blood flow and hence function. By improving systemic pressure, even if only marginally, there is likely to be a consequent beneficial effect on renal blood flow and excretory function.

In summary, the administration of albumin to cirrhotic animals was found to improve the status of the animal and prevent a number of the symptoms of the induced decompensation. Furthermore, the addition of an agent to remove endotoxin significantly improved the effects of albumin.

The invention claimed is:

1. An apparatus for the treatment of an individual having liver disease, comprising:
    (a) a membrane having a pore size of less than 100 kDa capable of removing albumin from the blood of an individual;
    (b) a means for removing endotoxin from the blood of the individual; and
    (c) a means for supplying albumin to the blood of the individual, wherein the supplied albumin is not derived from the individual; wherein (a) and (b) are separate components of the apparatus.

2. An apparatus according to claim 1, wherein the apparatus further comprises (d) a means for removing toxins bound to albumin from the blood of the individual.

3. An apparatus according to claim 1, wherein the means (b) comprises a solid support capable of removing endotoxin.

4. An apparatus according to claim 1, wherein the albumin in (c) is pharmaceutical grade albumin.

5. An apparatus according to claim 1, wherein the blood of the individual passes through the apparatus ex vivo.

6. An apparatus according to claim 1, wherein the membrane has a pore size of greater than 50 kDa.

7. An apparatus according to claim 1 wherein said membrane is a means for selectively removing albumin from the blood of the individual.

8. An apparatus according to claim 1 wherein the means (b) is an means for selectively removing endotoxin from the blood of the individual.

9. An apparatus according to claim 1 wherein said means (b) removes free endotoxin that is not bound to albumin.

10. A method of treating liver disease comprising the steps of contacting blood from an individual with an apparatus according to claim 1, such that albumin and endotoxin are removed from the blood of the individual.

11. A method according to claim 10, wherein the method is carried out ex vivo.

12. A method of treating liver disease in an individual comprising the steps of:
    (a) removing albumin from the blood of the individual;
    (b) reducing the level of endotoxin in the blood of the individual; and
    (c) introducing albumin to the blood of the individual, wherein the introduced albumin is not derived from the individual,
    wherein step (a) is carried out using a membrane having a pore size of less than 100 kDa; and wherein steps (a) and (b) comprise different means for removing albumin and reducing the level of endotoxin.

13. A method according to claim 12, wherein steps (a) and (c) are carried out by dialysis.

14. A method according to claim 12, wherein step (b) comprises removing endotoxin from the blood of the individual.

15. A method according to claim 12, wherein the method is carried out ex vivo.

16. A method according to claim 12, wherein step (b) comprises administering to the individual a therapeutically effective amount of an agent capable of reducing the level of endotoxin in the blood.

17. A method according to claim 12, wherein the albumin of step (c) is pharmaceutical grade albumin.

18. A method according to claim 12, wherein the method is carried out using an apparatus comprising:

(a) a membrane having a pore size of less than 100 kDa capable of removing albumin from the blood of the individual;
(b) a means for removing endotoxin from the blood of the individual; and
(c) a means for supplying albumin to the blood of the individual, wherein the supplied albumin is not derived from the individual; and wherein (a) and (b) are separate components of the apparatus.

19. A method according to claim 12 where step (b) removes free endotoxin that is not bound to albumin.

20. A method of treating blood extracorporeally by selectively removing albumin and endotoxin from the blood, wherein the blood is from an individual having liver disease, wherein the method comprises:
   (a) obtaining blood from an individual having liver disease;
   (b) incubating the blood with a solid support that removes albumin and thereby removing albumin from the blood;
   (c) incubating the blood with a separate solid support that removes endotoxin and thereby removing endotoxin from the blood; and
   (d) supplying albumin to the blood of the individual, wherein the supplied albumin is not derived from the individual.

21. A method according to claim 20 wherein said solid support of (b) removes free endotoxin that is not bound to albumin.

22. A method according to claim 12 comprising:
   (a) removing albumin from the blood of the individual and introducing albumin to the blood of the individual, wherein the introduced albumin is not derived from the individual, wherein said removing and introducing are carried out using a membrane having a pore size of less than 100 kDa; and
   (b) reducing the level of endotoxin in the blood of the individual;
   wherein step (b) comprises different means for reducing the level of endotoxin than the membrane in step (a).

23. A method according to claim 22 wherein step (b) removes free endotoxin that is not bound to albumin.

* * * * *

UNITED STATES PATENT AND TRADEMARK OFFICE
CERTIFICATE OF CORRECTION

PATENT NO. : 8,480,607 B2
APPLICATION NO. : 12/312028
DATED : July 9, 2013
INVENTOR(S) : Davies et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 745 days.

Signed and Sealed this
Eighth Day of September, 2015

Michelle K. Lee
*Director of the United States Patent and Trademark Office*